(12) United States Patent
Pedersen et al.

(10) Patent No.: US 7,341,983 B2
(45) Date of Patent: *Mar. 11, 2008

(54) ANTIMICROBIAL COMPOSITIONS INCLUDING CARBOXYLIC ACIDS AND ALKOXYLATED AMINES

(75) Inventors: Daniel E. Pedersen, Cottage Grove, MN (US); Steven E. Lentsch, St. Paul, MN (US); Jessica S. Hammerberg, Rosemount, MN (US); Brandon Herdt, Hastings, MN (US); Victor F. Man, St. Paul, MN (US)

(73) Assignee: Ecolab Inc., St. Paul, MN (US)

( * ) Notice: Subject to any disclaimer, the term of this patent is extended or adjusted under 35 U.S.C. 154(b) by 81 days.

This patent is subject to a terminal disclaimer.

(21) Appl. No.: 10/634,196

(22) Filed: Aug. 4, 2003

(65) Prior Publication Data

US 2005/0032668 A1    Feb. 10, 2005

(51) Int. Cl.
C11D 1/72    (2006.01)
C11D 1/722    (2006.01)
C11D 3/22    (2006.01)
C11D 3/30    (2006.01)

(52) U.S. Cl. ............... 510/383; 510/433; 510/437; 510/488; 510/499; 510/506; 422/28

(58) Field of Classification Search ........ 510/243, 510/336, 337, 341, 350, 351, 356, 319, 382, 510/383, 421, 423, 424, 499, 506, 488; 422/28
See application file for complete search history.

(56) References Cited

U.S. PATENT DOCUMENTS

| | | | |
|---|---|---|---|
| 4,895,667 A | 1/1990 | Fox et al. | |
| 5,234,719 A | 8/1993 | Richter et al. | |
| 5,436,008 A | 7/1995 | Richter et al. | |
| 5,962,399 A * | 10/1999 | Wulff et al. | 510/470 |
| 6,060,625 A | 5/2000 | Su et al. | |
| 6,063,145 A | 5/2000 | Larkin et al. | |
| 6,228,827 B1 * | 5/2001 | Penninger et al. | 510/320 |
| 6,350,725 B1 | 2/2002 | Levitt et al. | |
| 6,425,959 B1 * | 7/2002 | Man | 134/39 |
| RE37,866 E | 10/2002 | Wright et al. | |
| 6,593,283 B2 * | 7/2003 | Hei et al. | 510/214 |
| 6,616,303 B1 * | 9/2003 | Rosset | 362/293 |
| 2002/0119907 A1 * | 8/2002 | Baker et al. | 510/475 |
| 2003/0070692 A1 * | 4/2003 | Smith et al. | 134/6 |

FOREIGN PATENT DOCUMENTS

| | | |
|---|---|---|
| EP | 0 887 401 A1 | 12/1998 |
| WO | WO 95/04459 | 2/1995 |
| WO | WO 95/31100 | 11/1995 |
| WO | WO 00/41567 | 7/2000 |

OTHER PUBLICATIONS

Search Results for "Alkoxylated Etheramines" dated Apr. 29, 2003 prepared by Dan Pedersen.
Material Safety Data Sheet for Product/Trade Name: Entry, prepared by Wilbur Ellis, www.wecomsds/Entry.PM6, Aug. 1996.
"Ever Evolving Chemistry . . . Everlasting Quality", Tomah Products, Inc. (Jan. 1999).
International Search Report dated Sep. 24, 2004.

* cited by examiner

*Primary Examiner*—Gregory R. Del Cotto
(74) *Attorney, Agent, or Firm*—Merchant & Gould P.C.

(57) ABSTRACT

The present invention relates to antimicrobial compositions including carboxylic acids, such as fatty acid antimicrobial agents, and alkoxylated amines, and to methods using these compositions.

8 Claims, No Drawings

ANTIMICROBIAL COMPOSITIONS INCLUDING CARBOXYLIC ACIDS AND ALKOXYLATED AMINES

FIELD OF THE INVENTION

The present invention relates to antimicrobial compositions including carboxylic acids, such as fatty acid antimicrobial agents, and alkoxylated amines, and to methods using these compositions.

BACKGROUND OF THE INVENTION

Conventional mixtures of fatty acid antimicrobial agents coupled with glycols or amines result in complexing, which has decreased stability of the composition, decreased antimicrobial activity, and/or caused additional disadvantages. Developing a cloudy composition can indicate esterification of a fatty acid antimicrobial agent, which can be accompanied by loss of antimicrobial activity. For example, fatty acid antimicrobial agents can form esters with glycols. Such an esterified composition can turn cloudy and even undergo phase separation. Amines interact with fatty acids and form inactive salts.

There remains a need for compositions in which fatty acid antimicrobial agents can be effectively formulated with a coupling agent.

SUMMARY OF THE INVENTION

The present invention relates to antimicrobial compositions including carboxylic acids, such as fatty acid antimicrobial agents, and alkoxylated amines, and to methods using these compositions.

In an embodiment, the present compositions include carboxylic acid antimicrobial agent and alkoxylated amine. In an embodiment the carboxylic acid antimicrobial agent includes a fatty acid antimicrobial agent, such as octanoic acid. In an embodiment, the alkoxylated amine has Formula III:

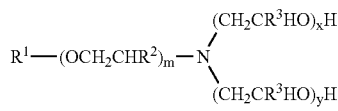

In an embodiment, the alkoxylated amine has Formula V:

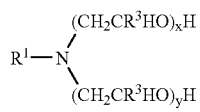

In certain embodiments, the composition can also include additional and optional ingredients, such as acidulant, surfactant, solvent, sequestrant, or mixtures thereof.

The present invention also includes a method of reducing the microbial population on an object. This method includes contacting the article with a composition including carboxylic acid antimicrobial agent and alkoxylated amine.

DETAILED DESCRIPTION OF THE INVENTION

Definitions

As used herein, the term "microorganisms" refers to any noncellular or unicellular (including colonial) organism. Microorganisms include all prokaryotes. Microorganisms include bacteria (including cyanobacteria and Mycobacteria), lichens, microfungi, protozoa, virinos, viroids, viruses, fungi (e.g., molds and yeast), and some algae. As used herein, the term "microbe" is synonymous with microorganism.

As used herein, the term "object" refers to something material that can be perceived by the senses, directly and/or indirectly. Objects include a surface, including a hard surface (such as glass, ceramics, metal, natural and synthetic rock, wood, and polymeric), an elastomer or plastic, woven and non-woven substrates, a food processing surface, a health care surface, and the like. Objects also include a food product (and its surfaces); a body or stream of water or a gas (e.g., an air stream); and surfaces and articles employed in hospitality and industrial sectors.

As used herein, the phrase "food processing surface" refers to a surface of a tool, a machine, equipment, a structure, a building, or the like that is employed as part of a food processing, preparation, or storage activity. Examples of food processing surfaces include surfaces of food processing or preparation equipment (e.g., slicing, canning, or transport equipment, including flumes), of food processing wares (e.g., utensils, dishware, wash ware, and bar glasses), and of floors, walls, or fixtures of structures in which food processing occurs. Food processing surfaces are found and employed in food anti-spoilage air circulation systems, aseptic packaging sanitizing, food refrigeration and cooler cleaners and sanitizers, ware washing sanitizing, blancher cleaning and sanitizing, food packaging materials, cutting board additives, third-sink sanitizing, beverage chillers and warmers, meat chilling or scalding waters, sanitizing gels, cooling towers, food processing antimicrobial garment sprays, and non-to-low-aqueous food preparation lubricants, oils, and rinse additives.

As used herein, the phrase "air streams" includes food anti-spoilage air circulation systems. Air streams also include air streams typically encountered in hospital, surgical, infirmity, birthing, mortuary, and clinical diagnosis rooms.

As used herein, the term "waters" includes food process or transport waters. Food process or transport waters include produce transport waters (e.g., as found in flumes, pipe transports, cutters, slicers, blanchers, retort systems, cooling towers, pools or fountains, pasteurizers, dental lines, produce spray applications for grocers, meat chillers, storefront collers, washers, and the like), belt sprays for food transport lines, boot and hand-wash dip-pans, third-sink rinse waters, and the like. Waters also include domestic and recreational waters such as pools, spas, recreational flumes and water slides, fountains, and the like.

As used herein, the phrase "health care surface" refers to a surface of an instrument, a device, a cart, a cage, furniture, a structure, a building, or the like that is employed as part of a health care activity. Examples of health care surfaces include surfaces of medical or dental instruments, of medical or dental devices, of electronic apparatus employed for monitoring patient health, and of floors, walls, or fixtures of structures in which health care occurs. Health care surfaces are found in hospital, surgical, infirmity, birthing, mortuary, and clinical diagnosis rooms. These surfaces can be those typified as "hard surfaces" (such as walls, floors, bed-pans, etc.,), or woven and non-woven surfaces (such as surgical garments, draperies, bed linens, bandages, etc.,), or patient-care equipment (such as respirators, diagnostic equipment, shunts, body scopes, wheel chairs, beds, etc.), or surgical and diagnostic equipment. Health care surfaces include articles and surfaces employed in animal health care.

As used herein, the term "instrument" refers to the various medical or dental instruments or devices that can benefit from cleaning with a high concentration composition according to the present invention.

As used herein, the phrases "medical instrument", "dental instrument", "medical device", "dental device", "medical equipment", or "dental equipment" refer to instruments, devices, tools, appliances, apparatus, and equipment used in medicine or dentistry. Such instruments, devices, and equipment can be cold sterilized, soaked or washed and then heat sterilized, or otherwise benefit from cleaning in a composition of the present invention. These various instruments, devices and equipment include, but are not limited to: diagnostic instruments, trays, pans, holders, racks, forceps, scissors, shears, saws (e.g. bone saws and their blades), hemostats, knives, chisels, rongeurs, files, nippers, drills, drill bits, rasps, burrs, spreaders, breakers, elevators, clamps, needle holders, carriers, clips, hooks, gouges, curettes, retractors, straightener, punches, extractors, scoops, keratomes, spatulas, expressors, trocars, dilators, cages, glassware, tubing, catheters, cannulas, plugs, stents, arthoscopes and related equipment, and the like, or combinations thereof.

As used herein, "agricultural" or "veterinary" objects or surfaces include animal feeds, animal watering stations and enclosures, animal quarters, animal veterinarian clinics (e.g. surgical or treatment areas), animal surgical areas, and the like.

As used herein, weight percent (wt-%), percent by weight, % by weight, and the like are synonyms that refer to the concentration of a substance as the weight of that substance divided by the weight of the composition and multiplied by 100.

As used herein, the term "about" modifying the quantity of an ingredient in the compositions of the invention or employed in the methods of the invention refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term about also encompasses amounts that differ due to different equilibrium or aging conditions for a composition resulting from a particular initial mixture. Whether or not modified by the term "about", the claims include equivalents to the quantities.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can effect two kinds of microbial cell damage. The first is a lethal, irreversible action resulting in complete microbial cell destruction or incapacitation. The second type of cell damage is reversible, such that if the organism is rendered free of the agent, it can again multiply. The former is termed bacteriocidal and the later, bacteriostatic. A sanitizer and a disinfectant are, by definition, agents which provide antibacterial or bacteriocidal activity. In contrast, a preservative is generally described as an inhibitor or bacteriostatic composition.

For the purpose of this patent application, successful reduction of microorganisms is achieved when the populations of microorganisms are reduced by at least about 0.3 $\log_{10}$., for example at least about 0.3-1 $\log_{10}$. In this application, such a population reduction is the minimum acceptable for the processes. Any increased reduction in population of microorganisms is an added benefit that provides higher levels of protection. For example, a 3 log or greater reduction is characteristic of a hard surface sanitizer. For example, a 5 log or greater reduction is characteristic of a food contact sanitizer.

Compositions Including Carboxylic Acids and Alkoxylated Amines

The present invention relates to antimicrobial compositions including carboxylic acids, such as antimicrobial agents, and alkoxylated amine. In an embodiment, the composition forms stable and clear concentrate compositions and retains antimicrobial activity. Certain embodiments of this composition can offer one or more of several advantages. In an embodiment, the present composition employs the alkoxylated amine to couple the carboxylic acid into an aqueous solvent. In an embodiment, the amine can couple the carboxylic acid into acidic compositions without complexing or reacting with the carboxylic acid. In an embodiment, the composition can form a clear and stable use solution. In an embodiment, the composition can retain the antimicrobial activity of the carboxylic acid. Advantageously, embodiments of the composition can provide effective soil removal.

Alkoxylated Amines

The present compositions can include any of a variety of alkoxylated amines. In an embodiment, the alkoxylated amine has general Formula I: $N(R_1)(R_2)(R_3)(R_4)$, in which at least one of $R_1$, $R_2$, or $R_3$ includes an alkoxylate or ether moiety. $R_4$ can be hydrogen, straight or branched alkyl, or straight or branched alkyl aryl. The alkoxylated amine can be a primary, secondary, or tertiary amine. In an embodiment, the alkoxylated amine is a tertiary amine. In an embodiment, each of $R_2$ and $R_3$ includes an alkoxylate moiety, e.g., one or more ethoxylate moieties, one or more propoxylate moieties, or combinations thereof, and $R_4$ is hydrogen. For example, one of $R_1$, $R_2$, or $R_3$ can include an ether moiety and the other two can include one or more ethoxylate moieties, one or more propoxylate moieties, or combinations thereof. In an embodiment, each of $R_1$, $R_2$, and $R_3$ includes an alkoxylate moiety, e.g., one or more ethoxylate moieties, one or more propoxylate moieties, or combinations thereof, and $R_4$ is hydrogen.

By way of further example, an alkoxylated amine can be represented by general Formulae Ia, IIb, or IIc, respectively:

$$R^5-(PO)_sN-(EO)_tH, \qquad\qquad \text{IIa}$$

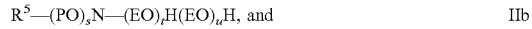

$$R^5-(PO)_sN-(EO)_tH(EO)_uH, \text{ and} \qquad \text{IIb}$$

$$R^5-N(EO)_tH; \qquad\qquad \text{IIc}$$

in which $R^5$ can be an alkyl, alkenyl or other aliphatic group, or an alkyl-aryl group of from 8 to 20 or from 12 to 14 carbon atoms, EO is oxyethylene, PO is oxypropylene, s is 1-20, 2-12, or 2 to 5, t is 1-20, 1-10, 2-12, or 2-5, and u is 1-20, 1-10, 2-12, or 2-5. Other variations on the scope of these compounds can be represented by formula IId:

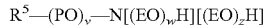

in which $R^5$ is as defined above, v is 1 to 20 (e.g., 1, 2, 3, or 4 or, in an embodiment, 2), and w and z are independently 1-20, 1-10, 2-12, or 2-5.

In an embodiment, the alkoxylated amine is an ether amine alkoxylate. An ether amine alkoxylate can have Formula III:

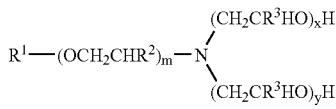

In Formula III, $R^1$ can be a straight or branched alkyl or alkylaryl; $R^2$ can independently in each occurrence be hydrogen or alkyl from 1 to 6 carbons; $R^3$ can independently in each occurrence be hydrogen or alkyl of from 1 to 6 carbons; m can average from about 1 to about 20; x and y can each independently average from 1 to about 20; and x+y can average from about 2 to about 40.

In an embodiment, in Formula III, $R^1$ can be: alkyl of from 8 to 24 carbon atoms, alkylaryl and contain from about 7 to about 30 carbon atoms, or alkylaryl (e.g., alkylaryl disubstituted with alkyl groups); $R^2$ can contain 1 or 2 carbon atoms or can be hydrogen; $R^3$ can be hydrogen, alkyl containing 1 or 2 carbons; and x+y can range from about 1 to about 3.

Such ether amine alkoxylates are described in U.S. Pat. Nos. 6,060,625 and 6,063,145, the disclosures of which are herein incorporated by reference.

In an embodiment, in Formula III, $R^1$ can be: alkyl of from 6 to 24 carbon atoms, alkylaryl and contain from about 7 to about 30 carbon atoms, or alkylaryl (e.g., alkylaryl disubstituted with alkyl groups); $R^2$ can contain 1 or 2 carbon atoms or can be hydrogen; $R^3$ can be hydrogen, alkyl containing 1 or 2 carbons; and x+y can range from about 1 to about 20.

In an embodiment, in Formula III, m can be 0 to about 20 and x and y can each independently average from 0 to about 20. In an embodiment, the alkoxy moieties can be capped or terminated with ethylene oxide, propylene oxide, or butylene oxide units.

In an embodiment, in Formula III, $R^1$ can be $C_6$-$C_{20}$ alkyl or $C_9$-$C_{13}$ alkyl, e.g., linear alkyl; $R^2$ can be $CH_3$; m can be about 1 to about 10; $R^3$ can be hydrogen; and x+y can range from about 5 to about 12. In an embodiment, such an ether amine alkoxylate can provide a clear use solution and a composition free of glycol ether.

In an embodiment, in Formula III, $R^1$ can be $C_6$-$C_{14}$ alkyl or $C_7$-$C_{14}$ alkyl, e.g., linear alkyl; $R^2$ can be $CH_3$; m can be about 1 to about 10; $R^3$ can be hydrogen; and x+y can range from about 2 to about 12. In an embodiment, such an ether amine alkoxylate can include alkoxylate moieties terminated with propylene oxide or butylene oxide units, which can provide low foam compositions.

In an embodiment, in Formula III, $R^1$ can be $C_6$-$C_{14}$ alkyl, e.g., linear alkyl; $R^2$ can be $CH_3$; m can be about 1 to about 10; $R^3$ can be hydrogen; and x+y can range from about 2 to about 20.

In an embodiment, the alkoxylated amine can be a $C_{12}$ to $C_{14}$ propoxy amine ethoxylate in which, in Formula III, $R^1$ can be $C_{12}$-$C_{14}$ alkyl, e.g., linear alkyl; $R^2$ can be $CH_3$; m can be about 10; $R^3$ can be hydrogen; x can be about 2.5, and y can be about 2.5.

In an embodiment, the alkoxylated amine can be a $C_{12}$ to $C_{14}$ propoxy amine ethoxylate in which, in Formula III, $R^1$ can be $C_{12}$-$C_{14}$ alkyl, e.g., linear alkyl; $R^2$ can be $CH_3$; m can be about 5; $R^3$ can be hydrogen; x can be about 2.5, and y can be about 2.5.

In an embodiment, the alkoxylated amine can be a $C_{12}$ to $C_{14}$ propoxy amine ethoxylate in which, in Formula III, $R^1$ can be $C_{12}$-$C_{14}$ alkyl, e.g., linear alkyl; $R^2$ can be $CH_3$; m can be about 2; $R^3$ can be hydrogen; x can be about 2.5, and y can be about 2.5.

In an embodiment, in Formula III, $R^1$ can be branched $C_{10}$ alkyl; $R^2$ can be $CH_2$; m can be 1; $R^3$ can be hydrogen; and x+y can be about 5. Such an alkoxylated amine can be a tertiary ethoxylated amine known as poly (5) oxyethylene isodecyloxypropylamine.

In an embodiment, in Formula III, $R^1$ can be branched $C_{13}$ alkyl; $R^2$ can be $CH_2$; m can be 1; and $R^3$ can be hydrogen. Such an alkoxylated amine can be a tertiary ethoxylated amine known as bis (2-hydroxyethyl) isotridecyl oxypropyl amine.

In an embodiment, in Formula III, $R^1$ can be linear $C_{12}$ alkyl, linear $C_{15}$ alkyl, or mixture thereof; $R^2$ can be $CH_2$; m can be 1; and $R^3$ can be hydrogen. Such an alkoxylated amine can be a tertiary ethoxylated amine known as poly (7) oxyethylene linear alkyl oxypropyl amine.

In an embodiment the alkoxylated amine can be a diamine that can be described by the formula R—O—CH2CH2CH2N(H)(CH2CH2CH2NH2) in which R is, for example, branched $C_{10}$ alkyl.

In an embodiment, the ether amine alkoxylate of Formula III is an ether amine ethoxylate propoxylate of Formula IV:

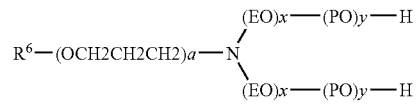

In Formula IV, $R^6$ can be a straight or branched alkyl or alkylaryl; a can average from about 1 to about 20; x and y can each independently average from 0 to about 10; and x+y can average from about 1 to about 20. Such an ether amine alkoxylate can be referred to as an ether amine ethoxylate propoxylate. In an embodiment, the alkoxy moieties can be capped or terminated with ethylene oxide, propylene oxide, or butylene oxide units.

In an embodiment, the alkoxylated amine can be a $C_{12}$ to $C_{14}$ propoxy amine ethoxylate that can be described by the formula: R-(PO)$_2$N[EO]$_{2.5}$-H[EO]$_{2.5}$—H. In an embodiment, the alkoxylated amine can be a $C_{12}$ to $C_{14}$ propoxy amine ethoxylate that can be described by the formula: R—(PO)$_{10}$N[EO]$_{2.5}$—H[EO]$_{2.5}$—H. In an embodiment, the alkoxylated amine can be a $C_{12}$ to $C_{14}$ propoxy amine ethoxylate that can be described by the formula: R—(PO)$_5$N[EO]$_{2.5}$—H[EO]$_{2.5}$—H. In an embodiment, the alkoxylated amine can be a tertiary ethoxylated amine known as poly (5) oxyethylene isodecyloxypropylamine, which has a branched $C_{10}H_{21}$ alkyl group off the ether oxygen. In an embodiment, the alkoxylated amine can be a diamine that can be described by the formula R—O—CH2CH2CH2N(H)(CH2CH2CH2NH2) in which R is branched $C_{10}$ alkyl. In an embodiment, the alkoxylated amine can be a tertiary ethoxylated amine known as iso-(2-hydroxyethyl) isodecyloxypropylamine, which has a branched $C_{10}H_{21}$ alkyl group off the ether oxygen.

Ether amine alkoxylates are commercially available, for example, under tradenames such as Surfonic (Huntsman Chemical) or Tomah Ether or Ethoxylated Amines.

In an embodiment, an ether amine alkoxylate can provide physical stability to the concentrate or use composition, retain the solubility and clarity of the concentrate or use solution, and/or not inhibit action of the antimicrobial agent. In an embodiment, the present composition includes ether amine alkoxylate as a or the primary solubilizing (coupling) or emulsifying agent.

In an embodiment, the alkoxylated amine is an alkyl amine alkoxylate. A suitable alkyl amine alkoxylate can have Formula V:

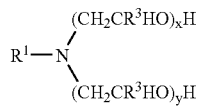

In Formula V, $R^1$ can be a straight or branched alkyl or alkylaryl; $R^3$ can independently in each occurrence be hydrogen or alkyl of from 1 to 6 carbons; x and y can each independently average from 0 to about 25; and x+y can average from about 1 to about 50. In an embodiment, in Formula V, x and y can each independently average from 0 to about 10; and x+y can average from about 1 to about 20. In an embodiment, the alkoxy moieties can be capped or terminated with ethylene oxide, propylene oxide, or butylene oxide units.

In an embodiment, the alkyl amine alkoxylate of Formula V is an alkyl amine ethoxylate propoxylate of Formula VI:

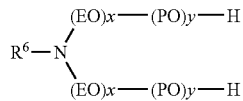

In Formula VI, $R^6$ can be a straight or branched alkyl or alkylaryl (e.g., C18 alkyl); x and y can each independently average from 0 to about 25; and x+y can average from about 1 to about 50. In an embodiment, in Formula VI, x and y can each independently average from 0 to about 10 or 20; and x+y can average from about 1 to about 20 or 40. Such an ether amine alkoxylate can be referred to as an amine ethoxylate propoxylate.

One such alkyl amine ethoxylate propoxylate can be described by the chemical names N,N-bis-2(omega-hydroxypolyoxyethylene/polyoxypropylene)ethyl alkylamine or N,N-Bis(polyoxyethylene/propylene) tallowalkylamine, by CAS number 68213-26-3, and/or by chemical formula $C_{64}H_{130}O_{18}$. In an embodiment, this alkyl amine ethoxylate propoxylate can be used as a mixture with another amine.

Alkyl amine alkoxylates are commercially available, for example, under tradenames such as Armoblen (Akzo Nobel). Armoblen 600 is called an alkylamine ethoxylate propoxylate.

In an embodiment, the alkoxylated amine is an ether amine. Suitable ether amines can have general Formula VII: $N(R_1)(R_2)(R_3)$, in which at least one of $R_1$, $R_2$, or $R_3$ includes an ether moiety. In an embodiment, $R_1$ includes an ether moiety and $R_2$, and $R_3$ are hydrogen. Such an ether amine can have Formula VIII:

$$R_4O(R_5)NH_2$$

In Formula VIII, $R_4$ can be $C_1$ to $C_{13}$ arylalkyl or alkyl, straight or branched chain and $R_5$ can be $C_1$ to $C_6$ alkyl, straight or branched chain.

Ether amines are commercially available, for example, from Tomah Products.

Suitable alkoxylated amines can include amines known as ethoxylated amine, propoxylated amine, ethoxylated propoxylated amine, alkoxylated alkyl amine, ethoxylated alkyl amine, propoxylated alkyl amine, ethoxylated propoxylated alkyl amine, ethoxylated propoxylated quaternary ammonium compound, ether amine (primary, secondary, or tertiary), ether amine alkoxylate, ether amine ethoxylate, ether amine propoxylate, alkoxylated ether amine, alkyl ether amine alkoxylate, alkyl propoxyamine alkoxylate, alkylalkoxy ether amine alkoxylate, and the like.

The alkoxylated amine can be present in the composition at about 0.01 to about 5 wt-%, about 0.02 to about 3 wt-%, about 0.03 to about 0.3 wt-%, about 0.1 to about 10 wt-%, about 0.2 to about 70 wt-%, about 0.3 to about 30 wt-%, about 0.4 to about 20 wt-%, about 1 to about 60 wt-%, about 1 to about 20 wt-%, about 1 to about 3 wt-%, about 1.5 to about 60 wt-%, about 1.5 to about 30 wt-%, about 2 to about 40 wt-%, about 2 to about 12 wt-%, about 3 to about 60 wt-%, about 3 to about 12 wt-%, about 4 to about 8 wt-%, about 5 to about 30 wt-%, about 10 to about 45 wt-%, about 10 to about 20 wt-%, or about 15 to about 30 wt-%. The alkoxylated amine can be present in the composition at about 0.2 to about 70 wt-%, about 0.3 to about 30 wt-%, or about 0.4 to about 20 wt-%. The alkoxylated amine can be present in the composition at about 1.5 to about 60 wt-%, about 1.5 to about 30 wt-%, or about 3 to about 12 wt-%. The alkoxylated amine can be present in the composition at about 1 to about 60 wt-%, about 1.5 to about 30 wt-%, or about 3 to about 12 wt-%. The alkoxylated amine can be present in the composition at about 2 to about 40 wt-%, about 5 to about 30 wt-%, or about 10 to about 20 wt-%. The alkoxylated amine can be present in the composition at about 3 to about 60 wt-%, about 10 to about 45 wt-%, or about 15 to about 30 wt-%. The alkoxylated amine can be present in the composition at about 1 to about 20 wt-%, about 2 to about 12 wt-%, or about 4 to about 8 wt-%. The alkoxylated amine can be present at any of these amounts not as part of a range and/or at any of these amounts not modified by about.

A ready to use or use composition according to the present invention can include alkoxylated amine at about 0.01 to about 5 wt-%, about 0.02 to about 3 wt-%, about 1 to about 3 wt-%, or about 0.03 to about 0.3 wt-%. The alkoxylated amine can be present at any of these amounts not as part of a range and/or at any of these amounts not modified by about.

Antimicrobial Agent

The present compositions can include an antimicrobial agent such as a lipid, a fatty or an oily, and/or a low HLB type antimicrobial agent. Suitable antimicrobial agents include carboxylic acid antimicrobial agents. Carboxylic acid antimicrobial agents include so-called fatty acid antimicrobial agents.

Suitable fatty acid antimicrobial agents include an aliphatic or aromatic fatty acid, either saturated or unsaturated, having from about 6 to about 20 carbon atoms, or mixtures of these fatty acids. In an embodiment, the aliphatic fatty acid is saturated. In an embodiment the fatty acid includes about 8 to about 14 carbon atoms. In an embodiment the fatty acid includes about 8 to about 12 carbon atoms. The fatty acid can be linear, branched or cyclic and can contain substituent atoms such as hydroxyl groups or ether linkages as long as the substituents do not affect antimicrobial activity. Suitable fatty acids include, for example, hexanoic acid, heptanoic acid, octanoic acid, nonanoic acid, decanoic acid, dodecanoic acid, myristic acid, or mixtures thereof. In an embodiment, the fatty acid includes heptanoic acid, octanoic acid, nonanoic acid, decanoic acid, dodecanoic acid, or mixtures thereof. In an embodiment, the fatty acid includes heptanoic acid, octanoic acid, nonanoic acid, decanoic acid, or mixtures thereof. In an embodiment, the fatty acid includes octanoic acid, nonanoic acid, decanoic acid, or mixtures thereof.

In an embodiment, the composition includes alkoxylated amine and fatty acid antimicrobial agent at a ratio, for example, in the range of about 1:1 to about 9:1 (alkoxylated amine:fatty acid antimicrobial agent), about 2:1 to about 6:1, about 2.5:1 to about 3.5:1, or about 3:1; about 2:1, about 2.5:1, about 3:1, about 3.5:1, about 4:1, about 4.5:1, or about 5:1; or about 3:1.

The present compositions include amounts of antimicrobial agent that provide effective antimicrobial use compositions. The antimicrobial agent can be present in the composition at about 0.005 to about 20 wt-%, about 0.01 to about 20 wt-%, about 0.01 to about 5 wt-%, about 0.015 to about 3 wt-%, about 0.02 to about 2 wt-%, about 0.03 to about 0.3 wt-%, about 0.05 to about 15 wt-%, about 0.1 to about 35 wt-%, about 0.1 to about 20 wt-%, about 0.1 to about 10 wt-%, about 0.2 to about 15 wt-%, about 0.2 to about 10 wt-%, about 0.3 to about 20 wt-%, about 0.5 to about 20 wt-%, about 0.5 to about 10 wt-%, about 0.5 to about 5 wt-%, about 1 to about 20 wt-%, about 1 to about 5 wt-%, about 1 to about 4 wt-%, about 2 to about 15 wt-%, or about 5 to about 10 wt-%. The antimicrobial agent can be present in the composition at about 0.1 to about 35 wt-%, about 0.2 to about 15 wt-%, or about 0.2 to about 10 wt-%. The antimicrobial agent can be present in the composition at about 0.3 to about 20 wt-%, about 0.5 to about 10 wt-%, or about 1 to about 4 wt-%. The antimicrobial agent can be present in the composition at about 0.5 to about 20 wt-%, about 0.5 to about 10 wt-%, or about 1 to about 4 wt-%. The antimicrobial agent can be present at any of these amounts not as part of a range and/or at any of these amounts not modified by about.

Suitable use compositions can include antimicrobial agent, such as octanoic acid, at concentrations of about 50 to about 3000 ppm, about 100 to about 2000 ppm, about 200 to about 1600 ppm, about 900 to about 1600 ppm, about 200 to about 600 ppm, about 100 to about 300 ppm, or the like.

A ready to use or use composition according to the present invention can include antimicrobial agent at about 0.005 to about 20 wt-%, about 0.01 to about 20 wt-%, about 0.01 to about 5 wt-%, about 0.02 to about 2 wt-%, about 0.015 to about 3 wt-%, about 0.03 to about 0.3 wt-%, or about 1 to about 5 wt-%. The antimicrobial agent can be present at any of these amounts not as part of a range and/or at any of these amounts not modified by about.

Acids or Acidulants

The present compositions can include one or more ingredient to decrease the pH, e.g. one or more acids or acidulants. Suitable acids include organic and inorganic acids. For example, suitable inorganic acids include phosphoric acid, hydrochloric acid, nitric acid, sulfuric acid, sulfamic acid, mixtures thereof, or the like. For example, suitable organic acids include lactic acid, citric acid, propionic acid, acetic acid, hydroxyacetic acid, formic acid, glutaric acid, malic acid, hydroxy propionic acid, succinic acid, glutaric acid, adipic acid, fumaric acid, mixtures thereof, or the like. The organic acid can be a mixture of adipic, malic, and succinic acids sold under the tradename Sokalan. In an embodiment, the acid includes phosphoric acid, lactic acid, or a mixture thereof. In an embodiment, the acid includes phosphoric acid, lactic acid, hydroxyacetic acid, or a mixture thereof. In an embodiment, the acid includes citric acid, lactic acid, urea hydrochloride, or a mixture thereof.

The acidulant or acid can be present in the composition at about 0.01 to about 5 wt-%, about 0.03 to about 0.3 wt-%, about 0.1 to about 85 wt-%, about 0.1 to about 5 wt-%, about 0.2 to about 95 wt-%, about 0.3 to about 90 wt-%, about 0.3 to about 85 wt-%, about 0.3 to about 3 wt-%, about 1 to about 5 wt-%, about 5 to about 85 wt-%, about 5 to about 60 wt-%, about 10 to about 75 wt-%, about 10 to about 45 wt-%, about 15 to about 65 wt-%, about 20 to about 50 wt-%, about 25 to about 35 wt-%, about 50 to about 80 wt-%, about 60 to about 70 wt-%, or about 65 wt-%. The acidulant or acid can be present in the composition at about 5 to about 60 wt-%, about 10 to about 45 wt-%, or about 25 to about 35 wt-%. The acidulant or acid can be present in the composition at about 0.2 to about 95 wt-%, about 0.3 to about 90 wt-%, or about 0.3 to about 85 wt-%. The acidulant or acid can be present in the composition at about 50 to about 80 wt-%, about 60 to about 70 wt-%, or about 65 wt-%. The acidulant or acid can be present at any of these amounts not as part of a range and/or at any of these amounts not modified by about.

A ready to use or use composition according to the present invention can include acid or acidulant at about 0.01 to about 5 wt-%, about 0.03 to about 0.3 wt-%, about 0.1 to about 5 wt-%, about 0.3 to about 3 wt-%, or about 1 to about 5 wt-%. The acid or acidulant can be present at any of these amounts not as part of a range and/or at any of these amounts not modified by about.

Surfactant

The present compositions can include one or more surfactants. The surfactant or surfactant admixture can include nonionic, semi-polar nonionic, or anionic surface-active agents; or any combination thereof. Generally, the concentration of surfactant or surfactant mixture useful in compositions of the present invention fall in the range of from about 0.01 to about 30 wt-%, about 0.01 to about 5 wt-%, about 0.03 to about 0.3 wt-%, about 0.05 to about 20 wt-%, about 0.1 to about 20 wt-%, about 0.1 to about 10 wt-%, about 0.1 to about 5 wt-%, about 0.3 to about 3 wt-%, about 0.5 to about 15 wt-%, about 1 to about 30 wt-%, about 1 to about 20 wt-%, about 1 to about 10 wt-%, about 1 to about 5 wt-%, about 2 to about 20 wt-%, about 2 to about 10 wt-%, about 3 to about 7 wt-%, or about 5 to about 15 wt-%. Surfactant can be present at about 1 to about 20 wt-%, about 2 to about 10 wt-%, or about 3 to about 7 wt-%. Surfactant can be present at about 1 to about 30 wt-%, about 2 to about 20 wt-%, or about 5 to about 15 wt-%. These percentages can refer to percentages of the commercially available surfactant composition, which can contain solvents, dyes, odorants, and the like in addition to the actual surfactant. In this case, the percentage of the actual surfactant chemical can be less than the percentages listed. These percentages can refer to the percentage of the actual surfactant chemical.

Surfactant can be present at any of these amounts not as part of a range and/or at any of these amounts not modified by about.

A ready to use or use composition according to the present invention can include surfactant at about 0.01 to about 5 wt-%, about 0.03 to about 0.3 wt-%, about 0.1 to about 5 wt-%, about 0.3 to about 3 wt-%, or about 1 to about 5 wt-%. The surfactant can be present at any of these amounts not as part of a range and/or at any of these amounts not modified by about.

In an embodiment, the surfactant includes anionic surfactant, amphoteric surfactant, nonionic surfactant, or mixture thereof. In an embodiment, the surfactant includes a nonionic surfactant. In an embodiment, the nonionic surfactant includes alcohol alkoxylate, arylacyl alkoxylates, amine oxide, alkoxide condensates, EOPO block, reverse, and heteric polymer, or mixture thereof. In an embodiment, the nonionic surfactant includes C11 linear ethoxylate with 7 moles EO average, C11 linear ethoxylate with 3 moles EO average, or mixture thereof. Nonionic surfactant can be present in the composition at about 0.01 to about 30 wt-%, about 0.05 to about 20 wt-%, about 0.1 to about 10 wt-%, about 1 to about 30 wt-%, about 1 to about 20 wt-%, about 2 to about 20 wt-%, about 2 to about 10 wt-%, about 3 to about 7 wt-%, or about 5 to about 15 wt-%. The nonionic can be present in the composition at about 1 to about 20 wt-%, about 2 to about 10 wt-%, or about 3 to about 7 wt-%. The nonionic can be present in the composition at about 1 to about 30 wt-%, about 2 to about 20 wt-%, or about 5 to about 15 wt-%. Nonionic surfactant can be present at any of these amounts not as part of a range and/or at any of these amounts not modified by about.

In an embodiment, the surfactant includes a anionic surfactant. In an embodiment, the anionic surfactant includes alkyl sulfonate, alkylaryl sulfonate, alcohol alkoxylate carboxylate, sarcosinate, taurate, acyl amino acid, alkanoic ester, phosphate ester, sulfiric acid ester, salt or ester thereof, or mixture thereof. Anionic can be present in the composition at about 0.01 to about 30 wt-%, about 0.05 to about 20 wt-%, about 0.1 to about 10 wt-%, about 1 to about 30 wt-%, about 1 to about 20 wt-%, about 2 to about 20 wt-%, about 2 to about 10 wt-%, about 3 to about 7 wt-%, or about 5 to about 15 wt-%. The anionic can be present in the composition at about 1 to about 20 wt-%, about 2 to about 10 wt-%, or about 3 to about 7 wt-%. The anionic can be present in the composition at about 1 to about 30 wt-%, about 2 to about 20 wt-%, or about 5 to about 15 wt-%. Anionic surfactant can be present at any of these amounts not as part of a range and/or at any of these amounts not modified by about.

In an embodiment, the surfactant includes amphoteric surfactant. In an embodiment, the amphoteric surfactant includes acyl amino acid, N-alkyl amino acid, salt or ester thereof, or mixture thereof. Amphoteric surfactant can be present in the composition at about 0.01 to about 30 wt-%, about 0.05 to about 20 wt-%, about 0.1 to about 10 wt-%, about 1 to about 30 wt-%, about 1 to about 20 wt-%, about 2 to about 20 wt-%, about 2 to about 10 wt-%, about 3 to about 7 wt-%, or about 5 to about 15 wt-%. The amphoteric surfactant can be present in the composition at about 1 to about 20 wt-%, about 2 to about 10 wt-%, or about 3 to about 7 wt-%. The amphoteric surfactant can be present in the composition at about 1 to about 30 wt-%, about 2 to about 20 wt-%, or about 5 to about 15 wt-%. Amphoteric surfactant can be present at any of these amounts not as part of a range and/or at any of these amounts not modified by about.

Nonionic Surfactant

Nonionic surfactants useful in the invention are generally characterized by the presence of an organic hydrophobic group and an organic hydrophilic group and are typically produced by the condensation of an organic aliphatic, alkyl aromatic, fatty alcohol, or polyoxyalkylene hydrophobic compound with a hydrophilic alkaline oxide moiety which in common practice is ethylene oxide or a polyhydration product thereof, polyethylene glycol. Practically any hydrophobic compound having a hydroxyl, carboxyl, amino, or amido group with a reactive hydrogen atom can be condensed with ethylene oxide, or its polyhydration adducts, or its mixtures with alkoxylenes such as propylene oxide to form a nonionic surface-active agent. The length of the hydrophilic polyoxyalkylene moiety which is condensed with any particular hydrophobic compound can be readily adjusted to yield a water dispersible or water soluble compound having the desired degree of balance between hydrophilic and hydrophobic properties.

Useful nonionic surfactants in the present invention include:

1. Block polyoxypropylene-polyoxyethylene polymeric compounds based upon propylene glycol, ethylene glycol, glycerol, trimethylolpropane, and ethylenediamine as the initiator reactive hydrogen compound. Examples of polymeric compounds made from a sequential propoxylation and ethoxylation of initiator are commercially available under the trade names Pluronic® and Tetronic® manufactured by BASF Corp.

Pluronice compounds are difunctional (two reactive hydrogens) compounds formed by condensing ethylene oxide with a hydrophobic base formed by the addition of propylene oxide to the two hydroxyl groups of propylene glycol. This hydrophobic portion of the molecule weighs from about 1,000 to about 4,000. Ethylene oxide is then added to sandwich this hydrophobe between hydrophilic groups, controlled by length to constitute from about 10% by weight to about 80% by weight of the final molecule.

Tetronic® compounds are tetra-functional block copolymers derived from the sequential addition of propylene oxide and ethylene oxide to ethylenediamine. The molecular weight of the propylene oxide hydrotype ranges from about 500 to about 7,000; and, the hydrophile, ethylene oxide, is added to constitute from about 10% by weight to about 80% by weight of the molecule.

2. Condensation products of one mole of alkyl phenol wherein the alkyl chain, of straight chain or branched chain configuration, or of single or dual alkyl constituent, contains from about 8 to about 18 carbon atoms with from about 3 to about 50 moles of ethylene oxide. The alkyl group can, for example, be represented by diisobutylene, di-amyl, polymerized propylene, iso-octyl, nonyl, and di-nonyl. These surfactants can be polyethylene, polypropylene, and polybutylene oxide condensates of alkyl phenols. Examples of commercial compounds of this chemistry are available on the market under the trade names Igepal® manufactured by Rhone-Poulenc and Triton® manufactured by Union Carbide.

3. Condensation products of one mole of a saturated or unsaturated, straight or branched chain alcohol having from about 6 to about 24 carbon atoms with from about 2 to about 50 moles of ethylene oxide. The alcohol moiety can consist of mixtures of alcohols in the above delineated carbon range or it can consist of an alcohol having a specific number of carbon atoms within this range. Examples of like commercial surfactant are available under the trade names Neodol® manufactured by Shell Chemical Co., Tomahdol manufactured by Tomah³ Products, and Alfonic® manufactured by Vista Chemical Co.

4. Condensation products of one mole of saturated or unsaturated, straight or branched chain carboxylic acid having from about 8 to about 18 carbon atoms with from about 6 to about 50 moles of ethylene oxide. The acid moiety can consist of mixtures of acids in the above defined carbon atoms range or it can consist of an acid having a specific number of carbon atoms within the range. Examples of commercial compounds of this chemistry are available on the market under the trade names Nopalcol® manufactured by Henkel Corporation and Lipopeg® manufactured by Lipo Chemicals, Inc.

In addition to ethoxylated carboxylic acids, commonly called polyethylene glycol esters, other alkanoic acid esters formed by reaction with glycerides, glycerin, and polyhydric (saccharide or sorbitan/sorbitol) alcohols have application in this invention for specialized embodiments, particularly indirect food additive applications. All of these ester moieties have one or more reactive hydrogen sites on their molecule which can undergo further acylation or ethylene oxide (alkoxide) addition to control the hydrophilicity of these substances.

Examples of Nonionic Low Foaming Surfactants Include:

5. Compounds from (1) which are modified, essentially reversed, by adding ethylene oxide to ethylene glycol to provide a hydrophile of designated molecular weight; and, then adding propylene oxide to obtain hydrophobic blocks on the outside (ends) of the molecule. The hydrophobic portion of the molecule weighs from about 1,000 to about 3,100 with the central hydrophile including 10% by weight to about 80% by weight of the final molecule. These reverse Pluronics® are manufactured by BASF Corporation under the trade name Pluronic® R or L surfactants.

Likewise, the Tetronic® R surfactants are produced by BASF Corporation by the sequential addition of ethylene oxide and propylene oxide to ethylenediamine. The hydrophobic portion of the molecule weighs from about 2,100 to about 6,700 with the central hydrophile including 10% by weight to 80% by weight of the final molecule. 6. Compounds from groups (1), (2), (3) and (4) which are modified by "capping" or "end blocking" the terminal hydroxy group or groups (of multi-functional moieties) to reduce foaming by reaction with a small hydrophobic molecule such as propylene oxide, butylene oxide, benzyl chloride; and, short chain fatty acids, alcohols or alkyl halides containing from 1 to about 5 carbon atoms; and mixtures thereof. Also included are reactants such as thionyl chloride which convert terminal hydroxy groups to a chloride group. Such modifications to the terminal hydroxy group may lead to all-block, block-heteric, heteric-block or all-heteric nonionics.

Additional Examples of Effective Low Foaming Nonionics Include:

7. The alkylphenoxypolyethoxyalkanols of U.S. Pat. No. 2,903,486 issued Sep. 8, 1959 to Brown et al. and represented by the formula

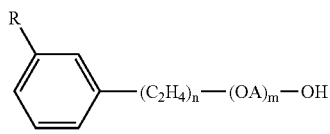

in which R is an alkyl group of 8 to 9 carbon atoms, A is an alkylene chain of 3 to 4 carbon atoms, n is an integer of 7 to 20, and m is an integer of 7 to 20.

The polyalkylene glycol condensates of U.S. Pat. No. 3,048,548 issued Aug. 7, 1962 to Martin et al. having alternating hydrophilic oxyethylene chains and hydrophobic oxypropylene chains where the weight of the terminal hydrophobic chains, the weight of the middle hydrophobic unit and the weight of the linking hydrophilic units each represent about one-third of the condensate.

The defoaming nonionic surfactants disclosed in U.S. Pat. No. 3,382,178 issued May 7, 1968 to Lissant et al. having the general formula $Z[(OR)_nOH]_z$ wherein Z is alkoxylatable material, R is a radical derived from an alkaline oxide which can be ethylene and propylene and n is an integer from, for example, 10 to 2,000 or more and z is an integer determined by the number of reactive oxyalkylatable groups.

The conjugated polyoxyalkylene compounds described in U.S. Pat. No. 2,677,700, issued May 4, 1954 to Jackson et al. corresponding to the formula $Y(C_3H_6O)_n(C_2H_4O)_mH$ wherein Y is the residue of organic compound having from about 1 to 6 carbon atoms and one reactive hydrogen atom, n has an average value of at least about 6.4, as determined by hydroxyl number and m has a value such that the oxyethylene portion constitutes about 10% to about 90% by weight of the molecule.

The conjugated polyoxyalkylene compounds described in U.S. Pat. No. 2,674,619, issued Apr. 6, 1954 to Lundsted et al. having the formula $Y[(C_3H_6O_n(C_2H_4O)_mH]_x$ wherein Y is the residue of an organic compound having from about 2 to 6 carbon atoms and containing x reactive hydrogen atoms in which x has a value of at least about 2, n has a value such that the molecular weight of the polyoxypropylene hydrophobic base is at least about 900 and m has value such that the oxyethylene content of the molecule is from about 10% to about 90% by weight. Compounds falling within the scope of the definition for Y include, for example, propylene glycol, glycerine, pentaerythritol, trimethylolpropane, ethylenediamine and the like.

Additional conjugated polyoxyalkylene surface-active agents which are advantageously used in the compositions of this invention correspond to the formula: $P[(C_3H_6O)_n(C_2H_4O)_mH]_x$ wherein P is the residue of an organic compound having from about 8 to 18 carbon atoms and containing x reactive hydrogen atoms in which x has a value of 1 or 2, n has a value such that the molecular weight of the polyoxyethylene portion is at least about 44 and m has a value such that the oxypropylene content of the molecule is from about 10% to about 90% by weight. In either case the oxypropylene chains may contain optionally, but advantageously, small amounts of ethylene oxide and the oxyethylene chains may contain also optionally, but advantageously, small amounts of propylene oxide.

8. Polyhydroxy fatty acid amide surfactants suitable for use in the present compositions include those having the structural formula $R^2CONR^1Z$ in which: R1 is H, $C_1$-$C_4$ hydrocarbyl, 2-hydroxy ethyl, 2-hydroxy propyl, ethoxy, propoxy group, or a mixture thereof; $R_2$ is a $C_5$-$C_{31}$ hydrocarbyl, which can be straight-chain; and Z is a polyhydroxyhydrocarbyl having a linear hydrocarbyl chain with at least 3 hydroxyls directly connected to the chain, or an alkoxylated derivative (preferably ethoxylated or propoxylated) thereof. Z can be derived from a reducing sugar in a reductive amination reaction; such as a glycityl moiety.

9. The alkyl ethoxylate condensation products of aliphatic alcohols with from 0 to about 25 moles of ethylene oxide are suitable for use in the present compositions. The alkyl chain of the aliphatic alcohol can either be straight or branched, primary or secondary, and generally contains from 6 to 22 carbon atoms.

10. The ethoxylated $C_6$-$C_{18}$ fatty alcohols and $C_6$-$C_{18}$ mixed ethoxylated and propoxylated fatty alcohols are suitable surfactants for use in the present compositions, particularly those that are water soluble. Suitable ethoxylated fatty alcohols include the $C_8$-$C_{18}$ ethoxylated fatty alcohols with a degree of ethoxylation of from 3 to 50.

11. Suitable nonionic alkylpolysaccharide surfactants, particularly for use in the present compositions include those disclosed in U.S. Pat. No. 4,565,647, Llenado, issued Jan. 21, 1986. These surfactants include a hydrophobic group containing from about 6 to about 30 carbon atoms and a polysaccharide, e.g., a polyglycoside, hydrophilic group containing from about 1.3 to about 10 saccharide units. Any reducing saccharide containing 5 or 6 carbon atoms can be used, e.g., glucose, galactose and galactosyl moieties can be substituted for the glucosyl moieties. (Optionally the hydrophobic group is attached at the 2-, 3-, 4-, etc. positions thus giving a glucose or galactose as opposed to a glucoside or galactoside.) The intersaccharide bonds can be, e.g., between the one position of the additional saccharide units and the 2-, 3-, 4-, and/or 6-positions on the preceding saccharide units.

12. Fatty acid amide surfactants suitable for use the present compositions include those having the formula: $R_6CON(R^7)_2$ in which $R^6$ is an alkyl group containing from 7 to 21 carbon atoms and each $R^7$ is independently hydrogen, $C_1$-$C_4$ alkyl, $C_1$-$C_4$ hydroxyalkyl, or —$(C_2H_4O)_xH$, where x is in the range of from 1 to 3.

Preferred nonionic surfactants for the compositions of the invention include alcohol alkoxylates, EO/PO block copolymers, alkylphenol alkoxylates, and the like.

The treatise *Nonionic Surfactants*, edited by Schick, M. J., Vol. 1 of the Surfactant Science Series, Marcel Dekker, Inc., New York, 1983 is an excellent reference on the wide variety of nonionic compounds generally employed in the practice of the present invention. A typical listing of nonionic classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch).

Semi-Polar Nonionic Surfactants

The semi-polar type of nonionic surface active agents are another class of nonionic surfactant useful in compositions of the present invention. Generally, semi-polar nonionics are high foamers and foam stabilizers, which can limit their application in CIP systems. However, within compositional embodiments of this invention designed for high foam cleaning methodology, semi-polar nonionics would have immediate utility. The semi-polar nonionic surfactants include the amine oxides, phosphine oxides, sulfoxides and their alkoxylated derivatives.

13. Amine oxides are tertiary amine oxides corresponding to the general formula:

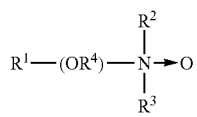

wherein the arrow is a conventional representation of a semi-polar bond; and, $R^1$, $R^2$, and $R^3$ may be aliphatic, aromatic, heterocyclic, alicyclic, or combinations thereof. Generally, for amine oxides of detergent interest, $R^1$ is an alkyl radical of from about 8 to about 24 carbon atoms; $R^2$ and $R^3$ are alkyl or hydroxyalkyl of 1-3 carbon atoms or a mixture thereof; $R^2$ and $R^3$ can be attached to each other, e.g. through an oxygen or nitrogen atom, to form a ring structure; $R^4$ is an alkaline or a hydroxyalkylene group containing 2 to 3 carbon atoms; and n ranges from 0 to about 20.

Useful water soluble amine oxide surfactants are selected from the octyl, coconut, or tallow alkyl di-(lower alkyl) amine oxides, specific examples of which are dodecyldimethylamine oxide, tridecyldimethylamine oxide, etradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl)amine oxide, 3,6,9-trioctadecyldimethylamine oxide and 3-dodecoxy-2-hydroxypropyldi-(2-hydroxyethyl)amine oxide.

Useful semi-polar nonionic surfactants also include the water soluble phosphine oxides having the following structure:

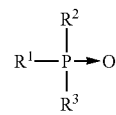

wherein the arrow is a conventional representation of a semi-polar bond; and, $R^1$ is an alkyl, alkenyl or hydroxyalkyl moiety ranging from 10 to about 24 carbon atoms in chain length; and, $R^2$ and $R^3$ are each alkyl moieties separately selected from alkyl or hydroxyalkyl groups containing 1 to 3 carbon atoms.

Examples of useful phosphine oxides include dimethyldecylphosphine oxide, dimethyltetradecylphosphine oxide, methylethyltetradecylphosphone oxide, dimethylhexadecylphosphine oxide, diethyl-2-hydroxyoctyldecylphosphine oxide, bis(2-hydroxyethyl)dodecylphosphine oxide, and bis (hydroxymethyl)tetradecylphosphine oxide.

Semi-polar nonionic surfactants useful herein also include the water soluble sulfoxide compounds which have the structure:

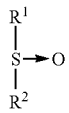

wherein the arrow is a conventional representation of a semi-polar bond; and, $R^1$ is an alkyl or hydroxyalkyl moiety of about 8 to about 28 carbon atoms, from 0 to about 5 ether linkages and from 0 to about 2 hydroxyl substituents; and $R^2$ is an alkyl moiety consisting of alkyl and hydroxyalkyl groups having 1 to 3 carbon atoms.

Useful examples of these sulfoxides include dodecyl methyl sulfoxide; 3-hydroxy tridecyl methyl sulfoxide;

3-methoxy tridecyl methyl sulfoxide; and 3-hydroxy-4-dodecoxybutyl methyl sulfoxide.

Preferred semi-polar nonionic surfactants for the compositions of the invention include dimethyl amine oxides, such as lauryl dimethyl amine oxide, myristyl dimethyl amine oxide, cetyl dimethyl amine oxide, combinations thereof, and the like.

Anionic Surfactants

Also useful in the present invention are surface active substances which are categorized as anionics because the charge on the hydrophobe is negative; or surfactants in which the hydrophobic section of the molecule carries no charge unless the pH is elevated to neutrality or above (e.g. carboxylic acids). Carboxylate, sulfonate, sulfate and phosphate are the polar (hydrophilic) solubilizing groups found in anionic surfactants. Of the cations (counter ions) associated with these polar groups, sodium, lithium and potassium impart water solubility; ammonium and substituted ammonium ions provide both water and oil solubility; and, calcium, barium, and magnesium promote oil solubility.

As those skilled in the art understand, anionics are excellent detersive surfactants and are therefore, favored additions to heavy duty detergent compositions. Generally, however, anionics have high foam profiles which limit their use alone or at high concentration levels in cleaning systems such as CIP circuits that require strict foam control. Anionics are very useful additives to preferred compositions of the present invention. Further, anionic surface active compounds are useful to impart special chemical or physical properties other than detergency within the composition. Anionics can be employed as gelling agents or as part of a gelling or thickening system. Anionics are excellent solubilizers and can be used for hydrotropic effect and cloud point control.

The majority of large volume commercial anionic surfactants can be subdivided into five major chemical classes and additional sub-groups known to those of skill in the art and described in "Surfactant Encyclopedia", *Cosmetics & Toiletries*, Vol. 104 (2) 71-86 (1989). The first class includes acylamino acids (and salts), such as acylgluamates, acyl peptides, sarcosinates (e.g. N-acyl sarcosinates), taurates (e.g. N-acyl taurates and fatty acid amides of methyl tauride), and the like. The second class includes carboxylic acids (and salts), such as alkanoic acids (and alkanoates), ester carboxylic acids (e.g. alkyl succinates), ether carboxylic acids, and the like. The third class includes phosphoric acid esters and their salts. The fourth class includes sulfonic acids (and salts), such as isethionates (e.g. acyl isethionates), alkylaryl sulfonates, alkyl sulfonates, sulfosuccinates (e.g. monoesters and diesters of sulfosuccinate), and the like. The fifth class includes sulfuric acid esters (and salts), such as alkyl ether sulfates, alkyl sulfates, and the like.

Anionic sulfate surfactants suitable for use in the present compositions include the linear and branched primary and secondary alkyl sulfates, alkyl ethoxysulfates, fatty oleyl glycerol sulfates, alkyl phenol ethylene oxide ether sulfates, the $C_5$—$C_{17}$ acyl—N—($C_1$—$C_4$ alkyl) and —N—($C_1$—$C_2$ hydroxyalkyl) glucamine sulfates, and sulfates of alkylpolysaccharides such as the sulfates of alkylpolyglucoside (the nonionic nonsulfated compounds being described herein).

Examples of suitable synthetic, water soluble anionic detergent compounds include the ammonium and substituted ammonium (such as mono-, di- and triethanolamine) and alkali metal (such as sodium, lithium and potassium) salts of the alkyl mononuclear aromatic sulfonates such as the alkyl benzene sulfonates containing from about 5 to about 18 carbon atoms in the alkyl group in a straight or branched chain, e.g., the salts of alkyl benzene sulfonates or of alkyl toluene, xylene, cumene and phenol sulfonates; alkyl naphthalene sulfonate, diamyl naphthalene sulfonate, and dinonyl naphthalene sulfonate and alkoxylated derivatives or their free acids.

Anionic carboxylate surfactants suitable for use in the present compositions include the alkyl ethoxy carboxylates, the alkyl polyethoxy polycarboxylate surfactants and the soaps (e.g. alkyl carboxyls). Secondary soap surfactants (e.g. alkyl carboxyl surfactants) useful in the present compositions include those which contain a carboxyl unit connected to a secondary carbon. The secondary carbon can be in a ring structure, e.g. as in p-octyl benzoic acid, or as in alkyl-substituted cyclohexyl carboxylates. The secondary soap surfactants typically contain no ether linkages, no ester linkages and no hydroxyl groups. Further, they typically lack nitrogen atoms in the head-group (amphiphilic portion). Suitable secondary soap surfactants typically contain 11-13 total carbon atoms, although more carbons atoms (e.g., up to 16) can be present.

Other anionic detergents suitable for use in the present compositions include olefin sulfonates, such as long chain alkene sulfonates, long chain hydroxyalkane sulfonates or mixtures of alkenesulfonates and hydroxyalkane-sulfonates. Also included are the alkyl sulfates, alkyl poly(ethyleneoxy) ether sulfates and aromatic poly(ethyleneoxy) sulfates such as the sulfates or condensation products of ethylene oxide and nonyl phenol (usually having 1 to 6 oxyethylene groups per molecule.

The particular salts will be suitably selected depending upon the particular formulation and the needs therein.

Further examples of suitable anionic surfactants are given in "Surface Active Agents and Detergents" (Vol. I and II by Schwartz, Perry and Berch). A variety of such surfactants are also generally disclosed in U.S. Pat. No. 3,929,678, issued Dec. 30, 1975 to Laughlin, et al. at Column 23, line 58 through Column 29, line 23.

Zwitterionic Surfactants

Zwitterionic surfactants can be thought of as a subset of the amphoteric surfactants. Zwitterionic surfactants can be broadly described as derivatives of secondary and tertiary amines, derivatives of heterocyclic secondary and tertiary amines, or derivatives of quaternary ammonium, quaternary phosphonium or tertiary sulfonium compounds. Typically, a zwitterionic surfactant includes a positive charged quaternary ammonium or, in some cases, a sulfonium or phosphonium ion; a negative charged carboxyl group; and an alkyl group. Zwitterionics generally contain cationic and anionic groups which ionize to a nearly equal degree in the isoelectric region of the molecule and which can develop strong" inner-salt" attraction between positive-negative charge centers. Examples of such zwitterionic synthetic surfactants include derivatives of aliphatic quaternary ammonium, phosphonium, and sulfonium compounds, in which the aliphatic radicals can be straight chain or branched, and wherein one of the aliphatic substituents contains from 8 to 18 carbon atoms and one contains an anionic water solubilizing group, e.g., carboxy, sulfonate, sulfate, phosphate, or phosphonate. Betaine and sultaine surfactants are exemplary zwitterionic surfactants for use herein.

A general formula for these compounds is:

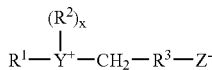

wherein $R^1$ contains an alkyl, alkenyl, or hydroxyalkyl radical of from 8 to 18 carbon atoms having from 0 to 10 ethylene oxide moieties and from 0 to 1 glyceryl moiety; Y is selected from the group consisting of nitrogen, phosphorus, and sulfur atoms; $R^2$ is an alkyl or monohydroxy alkyl group containing 1 to 3 carbon atoms; x is 1 when Y is a sulfur atom and 2 when Y is a nitrogen or phosphorus atom, $R^3$ is an alkylene or hydroxy alkylene or hydroxy alkylene of from 1 to 4 carbon atoms and Z is a radical selected from the group consisting of carboxylate, sulfonate, sulfate, phosphonate, and phosphate groups.

Examples of zwitterionic surfactants having the structures listed above include: 4-[N,N-di(2-hydroxyethyl)-N-octadecylammonio]-butane-1-carboxylate; 5-[S-3-hydroxypropyl-S-hexadecylsulfonio]-3-hydroxypentane-1-sulfate; 3-[P,P-diethyl-P-3,6,9-trioxatetracosanephosphonio]-2-hydroxypropane-1-phosphate; 3-[N,N-dipropyl-N-3-dodecoxy-2-hydroxypropyl-ammonio]-propane-1-phosphonate; 3-(N,N-dimethyl-N-hexadecylammonio)-propane-1-sulfonate; 3-(N,N-dimethyl-N-hexadecylammonio)-2-hydroxy-propane-1-sulfonate; 4-[N,N-di(2(2-hydroxyethyl)-N(2-hydroxydodecyl)ammonio]-butane-1-carboxylate; 3-[S-ethyl-S-(3-dodecoxy-2-hydroxypropyl)sulfonio]-propane-1-phosphate; 3-[P,P-dimethyl-P-dodecylphosphonio]-propane-1-phosphonate; and S[N,N-di(3-hydroxypropyl)-N-hexadecylammonio]-2-hydroxy-pentane-1-sulfate. The alkyl groups contained in said detergent surfactants can be straight or branched and saturated or unsaturated.

The zwitterionic surfactant suitable for use in the present compositions includes a betaine of the general structure:

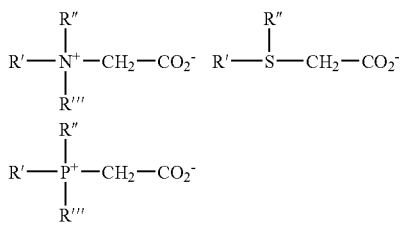

These surfactant betaines typically do not exhibit strong cationic or anionic characters at pH extremes nor do they show reduced water solubility in their isoelectric range. Unlike "texternal" quaternary ammonium salts, betaines are compatible with anionics. Examples of suitable betaines include coconut acylamidopropyldimethyl betaine; hexadecyl dimethyl betaine; $C_{12-14}$ acylamidopropylbetaine; $C_{8-14}$ acylamidohexyldiethyl betaine; 4-$C_{14-16}$ acylmethylamidodiethylammonio-1-carboxybutane; $C_{16-18}$ acylamidodimethylbetaine; $C_{12-16}$ acylamidopentanediethylbetaine; and $C_{12-16}$ acylmethylamidodimethylbetaine.

Sultaines useful in the present invention include those compounds having the formula $(R(R^1)_2 N^+R^2SO^{3-}$, in which R is a $C_6$-$C_{18}$ hydrocarbyl group, each $R^1$ is typically independently $C_1$-$C_3$ alkyl, e.g. methyl, and $R^2$ is a $C_1$-$C_6$ hydrocarbyl group, e.g. a $C_1$-$C_3$ alkylene or hydroxyalkylene group.

A typical listing of zwitterionic classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch).

In an embodiment, the composition of the present invention includes a betaine. For example, the composition can include cocoamidopropyl betaine. The betaine can be present in the composition at about 0.01 to about 30 wt-%, about 0.05 to about 20 wt-%, or about 0.1 to about 10 wt-%.

Solvent

The present compositions can include one or more solvents. Suitable solvents include organic and aqueous solvents. For example, suitable organic solvents include isopropanol, other lower alcohols, glycol ethers, mixtures thereof, or the like. For example, suitable aqueous solvents include water, mixtures of water with the organic solvent, mixtures thereof, or the like. In an embodiment, the solvent includes isopropanol, water, or a mixture thereof.

The solvent can be present in the composition at about 0.01 to about 10 wt-%, about 0.1 to about 5 wt-%, about 0.5 to about 2.5 wt-%, about 0.01 to about 1.0 wt-%, about 0.1 to about 2.5 wt-%, about 0.5 to about 5 wt-%, about 1 to about 20 wt-%, about 1 to about 10 wt-%, about 2 to about 10 wt-%, or about 3 to about 7 wt-%. The solvent can be present in the composition at about 1 to about 20 wt-%, about 2 to about 10 wt-%, or about 3 to about 7 wt-%. The solvent (particularly a solvent like water, which can be employed as a diluent) can be present in the composition at about 0.01 to about 99 wt-%, about 0.1 to about 99 wt-%, about 1 to about 80 wt-%, or about 10 to about 70 wt-%. Solvent can be present at any of these amounts not as part of a range and/or at any of these amounts not modified by about.

Sequestrant

The present compositions can include one or more sequestrants. Suitable sequestrants include organic chelating compounds that sequester metal ions in solution, particularly transition metal ions. Such sequestrants include organic amino- or hydroxy-polyphosphonic acid complexing agents (either in acid or soluble salt forms), carboxylic acids, hydroxycarboxylic acids, or aminocarboxylic acids.

Chelating agents or sequestrants generally useful in the present compositions include salts or acids of (expressed in acid form) alkyl diamine polyacetic acid-type chelating agents such as ethylenediamine tetraacetic acid (EDTA), hydroxyethylethylethylene diamine triacetic acid (HEDTA), and ethylene triaminepentaacetic acid, phosphonic acid, and phosphonate-type chelating agents among others. Suitable phosphonic acids and phosphonate salts include 1-hydroxy ethylidene-1,1-diphosphonic acid ($CH_3C(PO_3H_2)_2OH$) (HEDP); ethylenediamine tetrakis methylenephosphonic acid (EDTMP); diethylenetriamine pentakis methylenephosphonic acid (DTPMP); cyclohexane-1,2-tetramethylene phosphonic acid; amino[tri(methylene phosphonic acid)]; (ethylene diamine[tetra methylene-phosphonic acid)]; 2-phosphene butane-1,2,4-tricarboxylic acid; as well as the alkyl metal salts, ammonium salts, or alkyloyl amine salts, such as mono, di, or tetra-ethanolamine salts.

Commercially available food additive chelating agents include phosphonates sold under the trade name DEQUEST® including, for example, 1-hydroxyethylidene-1,1-diphosphonic acid, available from Monsanto Industrial Chemicals Co., St. Louis, Mo., as DEQUEST® 2010; amino(tri(methylenephosphonic acid)), ($N[CH_2PO_3H_2]_3$), available from Monsanto as DEQUEST® 2000; ethylenediamine[tetra(methylenephosphonic acid)] available from Monsanto as DEQUEST® 2041; and 2-phosphonobutane-1,2,4-tricarboxylic acid available from Mobay Chemical Corporation, Inorganic Chemicals Division, Pittsburgh, Pa., as Bayhibit AM.

The above-mentioned phosphonic acids can also be used in the form of water soluble acid salts, particularly the alkali metal salts, such as sodium or potassium; the ammonium salts or the alkylol amine salts where the alkylol has 2 to 3 carbon atoms, such as mono-, di-, or triethanolamine salts. If desired, mixtures of the individual phosphonic acids or their acid salts can also be used.

In an embodiment, amino phosphate or phosphonate can be employed as a sequestrant. Suitable sequestrants can include ethylene diamine (tetramethylene phosphonates), nitrilotrismethylene phosphates, diethylenetriamine (pentamethylene phosphonates). These amino phosphonates commonly contain alkyl or alkaline groups with less than 8 carbon atoms. The phosphonic acid may also include a low molecular weight phosphonopolycarboxylic acid such as one having about 2-4 carboxylic acid moieties and about 1-3 phosphonic acid groups. Such acids include 1-phosphono-1-methylsuccinic acid, phosphonosuccinic acid and 2-phosphonobutane-1,2,4-tricarboxylic acid.

The concentrate composition can include sequestrant at a concentration of, for example, about 0.01 wt-% to about 15 wt-% of the composition, from about 0.1 wt-% to about 10 wt-% of the composition, or from about 0.2 wt-% to 5 wt-% of the composition.

Adjuvants

The present composition can also include any number of adjuvants. Specifically, the composition can include stabilizing agent, wetting agent, thickener, foaming agent, pigment or dye among any number of constituents which can be added to the composition. Such adjuvants can be preformulated with the present composition or added to the system simultaneously, or even after, the addition of the present composition. The composition can also contain any number of other constituents as necessitated by the application, which are known and which can facilitate the activity of the present compositions.

Defoaming Agents

The composition can also contain additional ingredients as necessary to assist in defoaming. Generally, defoamers which can be used in accordance with the invention include silica and silicones; aliphatic acids or esters; alcohols; sulfates or sulfonates; amines or amides; halogenated compounds such as fluorochlorohydrocarbons; vegetable oils, waxes, mineral oils as well as their sulfated derivatives; and phosphates and phosphate esters such as alkyl and alkaline diphosphates, and tributyl phosphates among others; and mixtures thereof.

Especially preferably, are those antifoaming agents or defoamers which are of food grade quality. To this end, one of the more effective antifoaming agents includes silicones. Silicones such as dimethyl silicone, glycol polysiloxane, methylphenol polysiloxane, trialkyl or tetralkyl silanes, hydrophobic silica defoamers and mixtures thereof can all be used in defoaming applications. Commercial defoamers commonly available include silicones such as Ardefoam® from Armour Industrial Chemical Company which is a silicone bound in an organic emulsion; Foam Kill® or Kresseo® available from Krusable Chemical Company which are silicone and non-silicone type defoamers as well as silicone esters; and Anti-Foam A® and DC-200 from Dow Coming Corporation which are both food grade type silicones among others. These defoamers can be present at a concentration range from about 0.01 wt-% to 5 wt-%, preferably from about 0.01 wt-% to 2 wt-%, and most preferably from about 0.01 wt-% to about 1 wt-%.

Thickening or Gelling Agents

Thickeners useful in the present invention include those compatible with acidic systems. Suitable thickeners can include those which do not leave contaminating residue on the surface of food product or food product processing apparatus. That is, preferred thickeners or gelling agents do not include components incompatible with food or other sensitive products in contact areas.

Generally, thickeners which may be used in the present invention include natural gums such as xanthan gum, guar gum, modified guar, or other gums from plant mucilage; polysaccharide based thickeners, such as alginates, starches, and cellulosic polymers (e.g., carboxymethyl cellulose, hydroxyethyl cellulose, and the like); polyacrylates thickeners; and hydrocolloid thickeners, such as pectin. Generally, the concentration of thickener employed in the present compositions or methods will be dictated by the desired viscosity within the final composition. However, as a general guideline, the viscosity of thickener within the present composition ranges from about 0.1 wt-% to about 3 wt-%, from about 0.1 wt-% to about 2 wt-%, or about 0.1 wt-% to about 0.5 wt-%.

Dyes and Fragrances

Various dyes, odorants including perfumes, and other aesthetic enhancing agents may also be included in the composition. Dyes may be included to alter the appearance of the composition, as for example, any of a variety of FD&C dyes, D&C dyes, and the like. Additional suitable dyes include Direct Blue 86 (Miles), Fastusol Blue (Mobay Chemical Corp.), Acid Orange 7 (American Cyanamid), Basic Violet 10 (Sandoz), Acid Yellow 23 (GAF), Acid Yellow 17 (Sigma Chemical), Sap Green (Keyston Analine and Chemical), Metanil Yellow (Keystone Analine and Chemical), Acid Blue 9 (Hilton Davis), Sandolan Blue/Acid Blue 182 (Sandoz), Hisol Fast Red (Capitol Color and Chemical), Fluorescein (Capitol Color and Chemical), Acid Green 25 (Ciba-Geigy), Pylakor Acid Bright Red (Pylam), and the like.

Fragrances or perfumes that may be included in the compositions include, for example, terpenoids such as citronellol, aldehydes such as amyl cinnamaldehyde, a jasmine such as C1S-jasmine or jasmal, vanillin, and the like.

Concentrate and Use Compositions

The compositions of the present invention can be formulated by combining the antimicrobially active materials, the alkoxylated amine, and any other ingredients. For example, these ingredients can be mixed to form a concentrate or superconcentrate composition, which can be diluted at the site of use to form a use composition.

Super concentrates do not include water as an purposefully added raw material (though water can be present in some of the ingredients). Superconcentrates can be formulated which are both flowable and stable and can be useful to provide small dispensed volumes or individual dosage packs.

The invention contemplates a concentrate composition which is diluted to a use solution prior to application to an object. Primarily for reasons of economics, the concentrate would normally be marketed and an end user would preferably dilute the concentrate with water or an aqueous diluent to a use solution.

The level of active components in the concentrate composition is dependent on the intended dilution factor and the desired activity of the fatty acid antimicrobial. Generally, a dilution of about 0.1 to about 25 ounces of concentrate composition per gallon of diluent (e.g., water) provides a suitable use composition. Higher use dilutions can be employed if elevated use temperature (greater than 25° C.) or extended exposure time (greater than 30 seconds) can be employed. In the typical use locus, the concentrate is diluted with a major proportion of water using commonly available tap or service water.

Embodiments of Compositions

In certain embodiments, the composition of the present invention can be described by the ingredients and amounts listed in the tables below.

TABLE A

| Ingredient | wt-% | wt-% | wt-% | wt-% | wt-% |
|---|---|---|---|---|---|
| Alkoxylated Amine | 0.2-70 | 0.3-30 | 0.4-20 | 1.5-60 | 1.5-30 |
| Fatty Acid Antimicrobial Agent | 0.1-35 | 0.2-15 | 0.2-10 | 0.3-20 | 0.5-10 |
| Alkoxylated Amine | 1-20 | 2-12 | 3-12 | 4-8 | |
| Fatty Acid Antimicrobial Agent | 0.5-20 | 0.5-10 | 1-4 | 1-4 | |

TABLE B

| Ingredient | wt-% | wt-% | wt-% |
|---|---|---|---|
| Alkoxylated Amine | 0.2-70 | 0.3-30 | 0.4-20 |
| Fatty Acid Antimicrobial Agent | 0.1-35 | 0.2-15 | 0.2-10 |

TABLE C

| Ingredient | wt-% | wt-% | wt-% |
|---|---|---|---|
| Alkoxylated Amine | 1.5-60 | 1.5-30 | 3-12 |
| Fatty Acid Antimicrobial Agent | 0.3-20 | 0.5-10 | 1-4 |

TABLE D

| Ingredient | wt-% | wt-% | wt-% |
|---|---|---|---|
| Alkoxylated Amine | 0.2-70 | 0.3-30 | 0.4-20 |
| Fatty Acid Antimicrobial Agent | 0.1-35 | 0.2-15 | 0.2-10 |
| Acidulant | 0.2-95 | 0.3-90 | 0.3-85 |

TABLE E

| Ingredient | wt-% | wt-% | wt-% |
|---|---|---|---|
| Alkoxylated Amine | 1-20 | 2-12 | 4-8 |
| Fatty Acid Antimicrobial Agent | 0.5-20 | 0.5-10 | 1-4 |
| Acidulant | 5-60 | 10-45 | 25-35 |
| Surfactant | 1-20 | 2-10 | 3-7 |

TABLE F

| Ingredient | wt-% | wt-% | wt-% |
|---|---|---|---|
| Alkoxylated Amine | 1-60 | 1.5-30 | 3-12 |
| Fatty Acid Antimicrobial Agent | 0.3-20 | 0.5-10 | 1-4 |
| Acidulant | 5-60 | 10-45 | 25-35 |
| Surfactant | 1-20 | 2-10 | 3-7 |

TABLE G

| Ingredient | wt-% | wt-% | wt-% |
|---|---|---|---|
| Alkoxylated Amine | 1-20 | 2-12 | 4-8 |
| Fatty Acid Antimicrobial Agent | 0.5-20 | 0.5-10 | 1-4 |
| Acidulant | 5-60 | 10-45 | 25-35 |
| Organic Solvent | 1-20 | 2-10 | 3-7 |

TABLE H

| Ingredient | wt-% | wt-% | wt-% |
|---|---|---|---|
| Alkoxylated Amine | 1-60 | 1.5-30 | 3-12 |
| Fatty Acid Antimicrobial Agent | 0.3-20 | 0.5-10 | 1-4 |
| Acidulant | 5-60 | 10-45 | 25-35 |
| Organic Solvent | 1-20 | 2-10 | 3-7 |

In certain embodiment, the present compositions can be provided as a superconcentrate. Superconcentrates can have the quantities of ingredients listed in the tables below.

TABLE I

| Ingredient | Wt % | Wt % | Wt % |
|---|---|---|---|
| Acidulant | 50-80 | 60-70 | about 65 |
| Fatty Acid Antimicrobial Agent | 1-20 | 2-15 | 5-10 |
| Alkoxylated Amine | 2-40 | 5-30 | 10-20 |
| Surfactant | 1-30 | 2-20 | 5-15 |

TABLE J

| Ingredient | Wt % | Wt % | Wt % |
|---|---|---|---|
| Acidulant | 50-80 | 60-70 | about 65 |
| Fatty Acid Antimicrobial Agent | 1-20 | 2-15 | 5-10 |
| Alkoxylated Amine | 3-60 | 10-45 | 15-30 |
| Surfactant | 1-30 | 2-20 | 5-15 |

In an embodiment, the present composition includes fatty acid antimicrobial agent, alkoxylated amine (which can function as a solubilizer or coupler), and a surfactant or mixture of surfactants. The surfactant or mixture of surfactant can be selected to provide effective soil removal. In an embodiment, the surfactant mixture includes a low HLB and fairly high HLB surfactant for additional cleaning. The composition can also include an acid, which can provide water hardness solubility and/or neutralize the amino functionality.

Methods Employing the Present Compositions

The compositions of the invention can be used for a variety of domestic or industrial applications, e.g., to reduce microbial or viral populations on a surface or object or in a body or stream of water. The compositions can be applied in a variety of areas including kitchens, bathrooms, factories, hospitals, dental offices and food plants, and can be applied to a variety of hard or soft surfaces having smooth, irregular or porous topography. Suitable hard surfaces include, for example, architectural surfaces (e.g., floors, walls, windows, sinks, tables, counters and signs); eating utensils; hard-surface medical or surgical instruments and devices; and hard-surface packaging. Such hard surfaces can be made from a variety of materials including, for example, ceramic, metal, glass, wood or hard plastic. Suitable soft surfaces include, for example paper; filter media, hospital and surgical linens and garments; soft-surface medical or surgical instruments and devices; and soft-surface packaging. Such soft surfaces can be made from a variety of materials including, for example, paper, fiber, woven or nonwoven fabric, soft plastics and elastomers. The compositions of the invention can also be applied to soft surfaces such as food and skin.

The antimicrobial compositions of the invention can be included in products such as sterilants, sanitizers, disinfectants, preservatives, deodorizers, antiseptics, fungicides, germicides, sporicides, virucides, detergents, bleaches, hard surface cleaners, hand soaps and pre- or post-surgical scrubs.

The antimicrobial compositions can also be used in veterinary products such as mammalian skin treatments or in products for sanitizing or disinfecting animal enclosures, pens, watering stations, and veterinary treatment areas such as inspection tables and operation rooms.

The present compositions can be employed for reducing the population of pathogenic microorganisms, such as pathogens of humans, animals, and the like. The compositions can exhibit activity against pathogens including fungi, molds, bacteria, spores, and viruses, for example, *S. aureus, E. coli, Streptococci, Legionella, Pseudomonas aeruginosa,* mycobacteria, or the like. Such pathogens can cause a varieties of diseases and disorders, including Mastitis or other mammalian milking diseases, tuberculosis, and the like. The compositions of the present invention can reduce the population of microorganisms on skin or other external or mucosal surfaces of an animal. In addition, the present compositions can kill pathogenic microorganisms that spread through transfer by water, air, or a surface substrate. The composition need only be applied to the skin, other external or mucosal surfaces of an animal water, air, or surface.

The antimicrobial compositions can also be used on foods and plant species to reduce surface microbial populations; used at manufacturing or processing sites handling such foods and plant species; or used to treat process waters around such sites. For example, the compositions can be used on food transport lines (e.g., as belt sprays); boot and hand-wash dip-pans; food storage facilities; anti-spoilage air circulation systems; refrigeration and cooler equipment; beverage chillers and warmers, blanchers, cutting boards, third sink areas, and meat chillers or scalding devices. The compositions of the invention can be used to treat produce transport waters such as those found in flumes, pipe transports, cutters, slicers, blanchers, retort systems, washers, and the like. Particular foodstuffs that can be treated with compositions of the invention include eggs, meats, seeds, leaves, fruits and vegetables. Particular plant surfaces include both harvested and growing leaves, roots, seeds, skins or shells, stems, stalks, tubers, corms, fruit, and the like. The compositions may also be used to treat animal carcasses to reduce both pathogenic and non-pathogenic microbial levels.

The present composition is useful in the cleaning or sanitizing of containers, processing facilities, or equipment in the food service or food processing industries. The antimicrobial compositions have particular value for use on food packaging materials and equipment, and especially for cold or hot aseptic packaging. Examples of process facilities in which the composition of the invention can be employed include a milk line dairy, a continuous brewing system, food processing lines such as pumpable food systems and beverage lines, etc. Food service wares can be disinfected with the composition of the invention. For example, the compositions can also be used on or in ware wash machines, dishware, bottle washers, bottle chillers, warmers, third sink washers, cutting areas (e.g., water knives, slicers, cutters and saws) and egg washers. Particular treatable surfaces include packaging such as cartons, bottles, films and resins; dish ware such as glasses, plates, utensils, pots and pans; ware wash machines; exposed food preparation area surfaces such as sinks, counters, tables, floors and walls; processing equipment such as tanks, vats, lines, pumps and hoses (e.g., dairy processing equipment for processing milk, cheese, ice cream and other dairy products); and transportation vehicles. Containers include glass bottles, PVC or polyolefin film sacks, cans, polyester, PEN or PET bottles of various volumes (100 ml to 2 liter, etc.), one gallon milk containers, paper board juice or milk containers, etc.

The antimicrobial compositions can also be used on or in other industrial equipment and in other industrial process streams such as heaters, cooling towers, boilers, retort waters, rinse waters, aseptic packaging wash waters, and the like. The compositions can be used to treat microbes and odors in recreational waters such as in pools, spas, recreational flumes and water slides, fountains, and the like.

A filter containing the composition can reduce the population of microorganisms in air and liquids. Such a filter can remove water and air-born pathogens such as *Legionella*.

Other hard surface cleaning applications for the antimicrobial compositions of the invention include clean-in-place systems (CIP), clean-out-of-place systems (COP), washer-decontaminators, sterilizers, textile laundry machines, ultra and nano-filtration systems and indoor air filters. COP systems can include readily accessible systems including wash tanks, soaking vessels, mop buckets, holding tanks, scrub sinks, vehicle parts washers, non-continuous batch washers and systems, and the like.

Generally, the actual cleaning of the in-place system or other surface (i.e., removal of unwanted offal therein) is accomplished with a different material such as a formulated detergent which is introduced with heated water. After this cleaning step, the instant composition would be applied or introduced into the system at a use solution concentration in unheated, ambient temperature water. CIP typically employ flow rates on the order of about 40 to about 600 liters per minute, temperatures from ambient up to about 70° C., and contact times of at least about 10 seconds, more preferably about 30 to about 120 seconds. The present composition can remain in solution in cold (e.g., 40° F./4° C.) water and heated (e.g., 140° F./60° C.) water. Although it is not normally necessary to heat the aqueous use solution of the present composition, under some circumstances heating may be desirable to further enhance its antimicrobial activity. These materials are useful at any conceivable temperatures.

A method of sanitizing substantially fixed in-place process facilities includes the following steps. The use solution of the invention is introduced into the process facilities at a temperature in the range of about 4° C. to 60° C. After introduction of the use solution, the solution is held in a container or circulated throughout the system for a time sufficient to sanitize the process facilities (i.e., to kill undesirable microorganisms). After the surfaces have been sanitized by means of the present composition, the use solution is drained. Upon completion of the sanitizing step, the system optionally may be rinsed with other materials such as potable water. The composition is preferably circulated through the process facilities for 10 minutes or less.

The composition may also be employed by dipping food processing equipment into the use solution, soaking the equipment for a time sufficient to sanitize the equipment, and wiping or draining excess solution off the equipment, The composition may be further employed by spraying or wiping food processing surfaces with the use solution, keeping the surfaces wet for a time sufficient to sanitize the surfaces, and removing excess solution by wiping, draining vertically, vacuuming, etc.

The composition of the invention may also be used in a method of sanitizing hard surfaces such as institutional type equipment, utensils, dishes, health care equipment or tools, and other hard surfaces. The composition may also be employed in sanitizing clothing items or fabric which have become contaminated. The use solution is contacted with any of the above contaminated surfaces or items at use temperatures in the range of about 4° C. to 60° C., for a period of time effective to sanitize, disinfect, or sterilize the surface or item. For example, the concentrate composition can be injected into the wash or rinse water of a laundry machine and contacted with contaminated fabric for a time sufficient to sanitize the fabric. Excess solution can then be removed by rinsing or centrifuging the fabric.

The antimicrobial compositions can be applied to microbes or to soiled or cleaned surfaces using a variety of methods. These methods can operate on an object, surface, in a body or stream of water or a gas, or the like, by contacting the object, surface, body, or stream with a composition of the invention. Contacting can include any of numerous methods for applying a composition, such as spraying the composition, immersing the object in the composition, foam or gel treating the object with the composition, or a combination thereof.

A concentrate or use concentration of a composition of the present invention can be applied to or brought into contact with an object by any conventional method or apparatus for applying an antimicrobial or cleaning composition to an object. For example, the object can be wiped with, sprayed with, and/or immersed in the composition, or a use solution made from the composition. The composition can be sprayed or wiped onto a surface; the composition can be caused to flow over the surface, or the surface can be dipped into the composition. Contacting can be manual or by machine.

The present invention may be better understood with reference to the following examples. These examples are intended to be representative of specific embodiments of the invention, and are not intended as limiting the scope of the invention.

EXAMPLES

Example 1

Materials

Materials used in these examples include: Alkoxylated amine 1, a $C_{12}$ to $C_{14}$ propoxy amine ethoxylate that can be described by the formula: R—$(PO)_2N[EO]_{2.5}$—$H[EO]_{2.5}$—H. Alkoxylated amine 2, a $C_{12}$ to $C_{14}$ propoxy amine ethoxylate that can be described by the formula: R—$(PO)_{10}N[EO]_{2.5}$—$H[EO]_{2.5}$—H. Alkoxylated amine 3, a $C_{12}$ to $C_{14}$ propoxy amine ethoxylate that can be described by the formula: R—$(PO)_5N[EO]_{2.5}$-$H[EO]_{2.5}$-H. Alkoxylated amine 4, a tertiary ethoxylated amine known as poly (5) oxyethylene isodecyloxypropylamine, which has a branched $C_{10}H_2$, alkyl group off the ether oxygen. Alkoxylated amine 5, a diamine that can be described by the formula R—O—CH2CH2CH2N(H)(CH2CH2CH2NH2) in which R is branched $C_{10}$ alkyl. Alkoxylated amine 6, a tertiary ethoxylated amine known as iso-(2-hydroxyethyl) isodecyloxypropylamine, which has a branched $C_{10}H_{21}$ alkyl group off the ether oxygen.

Nonionic surfactants included: Tomadol 1-7 and Tomadol 1-3, each of which are C11 linear alcohol ethoxylates with 7 moles and 3 moles, respectively, average EO. Triton X-100, which has the structure octyl phenol 9-10 moles ethoxylate. NPE-15, which has the structure nonylphenol 15 mole ethoxylate. Rewoteric AMV, which has the formula capryloamphoglycinate sodium salt or 1H-imidazolium,1-(carboxymethyl)-2-heptyl-1-(2-hydroxethyl)-sodium salt. NPE 4.5, which has the structure nonylphenol 4.5 mole ethoxylate. Neodol 91-6, which has the structure C9-C11 alcohol 6 mole ethoxylate.

Test Compositions

Tables 1-5 list the ingredients and the amounts employed in several of the test compositions employed in Example 1. The various compositions were made by, for example, mixing the ingredients in the order listed. Unless indicated otherwise, mixing produced a clear, homogeneous solution. For use, the concentrate compositions were diluted by hand or with known dispensing equipment. The amounts of ingredients listed in the tables are given in wt-%.

TABLE 1

Embodiments of Compositions of the Invention

| | a | b | c | d | e | f | g | h |
|---|---|---|---|---|---|---|---|---|
| Soft water | 62 | 62 | 62 | 61 | 58 | 44 | 65 | 58 |
| Phosphoric acid, 75% | 21 | 21 | 21 | 21 | 21 | 27 | 20 | 21 |
| Citric acid, 50% | 8.0 | 8.0 | 8.0 | 8.0 | 8.0 | 11 | 8.0 | 8 |
| Octanoic acid | 2.4 | 2.4 | 2.4 | 2.4 | 2.4 | 3.2 | 2.4 | 2.4 |
| Alkoxylated Amine 1 | | 3.3 | 4.0 | | 5.0 | 6.7 | 4.5 | |
| Alkoxylated Amine 2 | | | | 5.4 | | | | |
| Alkoxylated Amine 3 | 4.0 | | | | | | | |
| Nonionic Surfactant | 3.0 | 3.0 | 3.0 | 3.1 | 5.0 | 6.7 | | 10.5 |
| Concentrate stability | clear | separated | clear | clear | clear | clear | clear | separated |

TABLE 1-continued

Embodiments of Compositions of the Invention

|  | a | b | c | d | e | f | g | h |
|---|---|---|---|---|---|---|---|---|
| Use solution clarity |  |  | clear | clear | clear | clear | clear |  |
| Stability of aged use solution | stable |  | stable | stable |  | stable |  |  |
| S. aureus kill | 20/20 |  | 20/20 |  | 60/60 | 60/60 | 20/20 |  |
| P. aeruginosa kill | 20/20 |  | 20/20 |  | 60/60 | 60/60 | 20/20 |  |

Alkoxylated amines 1-3 are described above under the heading Materials. All quantities were in wt-%.

TABLE 2

Embodiments of Compositions of the Invention

|  | i | j | k | l | m |
|---|---|---|---|---|---|
| Soft water | 57 | 57 | 57 | 50 | 66 |
| Phosphoric acid, 75% | 21 | 21 | 21 | 21 | 21 |
| Citric acid, 50% | 8.0 | 8.0 | 8.0 | 8.0 | 8.0 |
| Octanoic Acid | 2.4 | 2.4 | 2.4 | 2.4 | 2.4 |
| Alkoxylated Amine 1 | 7.2 |  |  |  |  |
| Alkoxylated Amine 4 |  | 7.2 |  |  |  |
| Alkoxylated Amine 5 |  |  | 7.2 | 4.8 |  |
| Alkoxylated Amine 6 |  |  |  |  | 4.5 |
| Nonionic Surfactant | 5.0 | 5.0 | 5.0 | 5.0 |  |
| Use solution clarity | clear | haze | haze | haze | cloudy |
| S. aureus kill | 20/20 | 20/20 | 20/20 | 20/20 | 20/20 |
| P. aeruginosa kill | 20/20 | 20/20 | 20/20 | 20/20 | 20/20 |

Alkoxylated amines 4-6 are described above under the heading Materials. All quantities were in wt-%.

TABLE 3

Embodiments of Compositions of the Invention

|  | n | o | p | q | r |
|---|---|---|---|---|---|
| Soft water | 58 | 58 | 43 | 43 | 43 |
| Phosphoric acid, 75% | 20 | 20 |  |  |  |
| Citric acid, 50% | 8.0 | 8.0 | 38 |  |  |
| Lactic Acid |  |  |  | 38 |  |
| Urea HCl |  |  |  |  | 38 |
| Octanoic Acid |  |  | 3.2 | 3.2 | 3.2 |
| Nonanoic Acid | 2.4 |  |  |  |  |
| Decanoic Acid |  | 2.4 |  |  |  |
| Alkoxylated Amine 1 | 5.3 | 5.8 | 6.7 | 6.7 | 6.7 |
| Nonionic Surfactant | 5.0 | 5.0 | 6.7 | 6.7 | 6.7 |
| Concentrate stability |  |  | clear | clear | clear |
| Use solution clarity | clear | slight haze/ clear | clear | clear | clear |
| Stability of aged use solution |  |  | stable | stable | stable |
| S. aureus kill | 20/20 | 20/20 |  |  |  |
| P. aeruginosa kill | 20/20 | 20/20 |  |  |  |

All quantities were in wt-%.

TABLE 4

Embodiments of Compositions of the Invention

|  | a2 | b2 | c2 | d2 | e2 | f2 | g2 | h2 | i2 |
|---|---|---|---|---|---|---|---|---|---|
| Soft water | 61 | 59 | 59 | 60 | 63 | 50 | 58 | 54 | 54 |
| Phosphoric acid, 75% | 20 | 21 | 21 | 22 | 21 | 21 | 21 | 21 | 20 |
| Citric acid, 50% | 8.0 | 8.0 | 8.0 | 8.7 | 8.0 | 8.0 | 8.0 | 8.0 | 8.0 |
| Octanoic acid | 2.4 | 2.4 | 2.5 | 2.6 | 2.5 | 2.4 | 2.4 | 2.4 | 2.4 |
| Propylene glycol N-propyl ether |  |  | 3.1 |  |  |  |  | 3.1 | 7.0 |
| Octylphenol ethoxylate (9-10 EO) | 3.0 | 4.8 | 3.1 | 3.3 | 3.0 |  |  | 4.8 |  |
| Nonylphenol ethoxylate (15 EO) | 3.0 |  | 3.1 |  |  |  |  |  |  |
| Capryloamphoglycinate sodium salt |  |  |  |  |  |  | 14 | 5.1 |  |
| C9-C11 alcohol ethoxylate (6 EO) |  |  |  |  |  |  | 6.0 |  |  |
| C11 alcohol ethoxylate (3 EO) |  |  |  |  |  |  |  |  |  |
| Alkoxylated Amine 3 | 2.2 | 5.1 | 0.58 |  |  | 5.1 |  |  |  |
| Alkoxylated Amine 4 |  |  |  | 3.0 | 3.5 |  |  |  |  |
| Secondary alcohol ethoxylate (20 EO) |  |  |  |  |  |  |  | 7.0 |  |
| Nonylphenol ethoxylate (4-5 EO) |  |  |  |  |  |  |  |  | 2.0 |
| Linear alkyl benzene sulfonic acid |  |  |  |  |  |  |  |  | 4.8 |
| Concentrate stability | separated | clear | clear | separated | clear/ yellow | clear | separated | clear | separated |

TABLE 4-continued

| | Embodiments of Compositions of the Invention | | | | | | | | |
|---|---|---|---|---|---|---|---|---|---|
| | a2 | b2 | c2 | d2 | e2 | f2 | g2 | h2 | i2 |
| Use solution clarity | | clear | hazy | | hazy | clear | | | |
| Stability of use solution | stable | stable | stable | | stable | stable | | | |
| S. aureus kill | 20/20 | 20/20 | 20/20 | | | 20/20 | | 0/20 | |
| P. aeruginosa kill | 20/20 | 20/20 | 20/20 | | | 20/20 | | | |

All quantities were in wt-%.

TABLE 5

Embodiments of Super Concentrate Compositions of the Invention

| | sc1 | sc2 | sc3 |
|---|---|---|---|
| Lactic acid, 88% | 69 | | 68 |
| Citric acid, 50% | | 69 | |
| Octanoic Acid | 5.7 | 5.7 | 9.5 |
| Alkoxylated Amine 1 | 12 | 12 | 23 |
| Nonionic Surfactant | 11 | 11 | |
| Clarity | clear | clear | clear |
| Stability | Stable | Stable | Stable |

All quantities were in wt-%.

Results

Test compositions were made with varying amounts and types of alkoxylated amines. These were made to include 2.4 wt-% octanoic acid, 21 wt-% phosphoric acid (75%), 8.0 wt-% citric acid, varying amounts of alkoxylated amine, with the remainder water. These compositions exhibited the solubilization efficiency profile shown in Table 6.

TABLE 6

Solution appearance with various types and amounts of alkoxylated amines.

| (wt-%) | Alkoxylated Amine 1 | Alkoxylated Amine 2 | Alkoxylated Amine 3 | Alkoxylated Amine 4 | Alkoxylated Amine 6 |
|---|---|---|---|---|---|
| 2.5 | — | — | — | clear/hazy | hazy yellow |
| 3 | — | milky white | — | hazy/clear | hazy yellow |
| 3.5 | separated | hazy white | milky white | hazy/clear | hazy |
| 4 | separated | milky white | separated | separated | milky yellow |
| 4.5 | clear | separated | clear | separated | opaque-yellow |
| 5 | clear | clear | clear | separated | separated |

The results in Table 6 indicate that clear compositions were obtained with 4.5 and 5 wt-% alkoxylated amines 1 and 2, which are described above under the heading Materials.

The results in Tables 1-5 indicate that additional compositions also yielded clear or hazy solutions with effective antimicrobial activity. The results for at least compositions a, b, e, f, g, j, n, b2, and f2 demonstrate that several alkoxylated amines provided clear and stable compositions at concentrations of about 4 to about 5.5 wt-%. Two of these compositions (e and f) were demonstrated to be effective disinfectants, exhibiting kill against two microbes in 60 of 60 tubes at concentrations of 8 oz composition per gallon.

Compositions including octanoic, nonanoic, or decanoic acids were clear and exhibited effective disinfectant activity. Disinfectant activity persisted in aged solutions. Compositions n and o included nonanoic acid and decanoic acid, respectively. The several acidulants tested (phosphoric acid, citric acid, lactic acid, and urea HCl, compositions n-r) all formed clear and stable use solutions and concentrates.

Example 2

Materials

The materials used in Example 2 include many of those used for the compositions of Example 1. Materials used in Example 2 include: Alkoxylated amine 7, an alkyl amine ethoxylate propoxylate described by the chemical names N,N-bis-2(omega-hydroxypolyoxyethylene/polyoxypropylene)ethyl alkylamine or N,N-bis(polyoxyethylene/propylene) tallowalkylamine, by CAS number 68213-26-3, and/or by chemical formula $C_{64}H_{130}O_{18}$., which can be in a mixture with another amine; Alkoxylated amine 8, Tomah E-17-2, bis (2-hydroxyethyl) isotridecyl oxypropyl amine; Alkoxylated amine 9, Tomah E-19-7, poly (7) oxyethylene linear alkyl oxypropyl amine with linear $C_{12}$ and $C_{15}$ alkyl chains; SXS (40%), sodium xylene sulfonate (40% solution); Tomah AO-455, low foaming amine oxide; Tomah Q-17-2 pg 74% active isotridecyloxypropyl bis (2-hydroxyethyl methyl amonium chloride) in propylene glycol; Tomah Q-17-2 ipa, 74% active isotridecyloxypropyl bis (2-hydroxyethyl methyl amonium chloride) in isopropanol; Tomah Q-14-2, 74% active isodecyl bis (2-hydroxyethyl methyl amonium chloride) in propylene glycol.

Test Compositions

Tables 7-9 list the ingredients and the amounts employed in several of the test compositions employed in Example 2. The various compositions were made by, for example, mixing the ingredients in the order listed. Unless indicated otherwise, mixing produced a clear, homogeneous solution. For use, the concentrate compositions were diluted by hand or with known dispensing equipment. The amounts of ingredients listed in the test compositions are given in wt-%.

TABLE 7

Embodiments of Compositions of the Invention

|  | 1 | 2 | 3 | 4 | 5 | 6 | 7 | 8 | 9 | 10 | 11 |
|---|---|---|---|---|---|---|---|---|---|---|---|
| Water | 50 | 47 | 45 | 42 | 40 | 37 | 45 | 42 | 40 | 37 | 35 |
| Phosphoric Acid (75%) | 35 | 35 | 35 | 35 | 35 | 35 | 35 | 35 | 35 | 35 | 35 |
| Lactic Acid (88%) | 5 | 5 | 5 | 5 | 5 | 5 | 5 | 5 | 5 | 5 | 5 |
| Dequest 2000 LC | 2.5 | 2.5 | 2.5 | 2.5 | 2.5 | 2.5 | 2.5 | 2.5 | 2.5 | 2.5 | 2.5 |
| PA-14 | 0 | 0 | 0 | 0 | 0 | 0 | 5 | 5 | 5 | 5 | 5 |
| Octanoic Acid | 3 | 6 | 3 | 6 | 3 | 6 | 3 | 6 | 3 | 6 | 3 |
| Alkoxylated Amine 7 | 0 | 0 | 5 | 5 | 10 | 10 | 0 | 0 | 5 | 5 | 10 |
| Isopropanol | 5 | 5 | 5 | 5 | 5 | 5 | 5 | 5 | 5 | 5 | 5 |

TABLE 8

Embodiments of Compositions of the Invention

|  | 12 | 13 | 14 | 15 | 16 | 17 | 18 | 19 | 20 |
|---|---|---|---|---|---|---|---|---|---|
| Water | 32 | 40 | 37 | 35 | 32 | 30 | 27 | 46 | 46 |
| Phosphoric Acid (75%) | 35 | 35 | 35 | 35 | 35 | 35 | 35 | 35 | 35 |
| Lactic Acid (88%) | 5 | 5 | 5 | 5 | 5 | 5 | 5 | 5 |  |
| Dequest 2000 LC | 2.5 | 2.5 | 2.5 | 2.5 | 2.5 | 2.5 | 2.5 | 2.5 | 2.5 |
| PA-14 | 5 | 10 | 10 | 10 | 10 | 10 | 10 | 2.5 | 2.5 |
| Octanoic Acid | 6 | 3 | 6 | 3 | 6 | 3 | 6 | 2 | 2 |
| Alkoxylated Amine 7 | 10 | 0 | 0 | 5 | 5 | 10 | 10 | 2.5 | 2.5 |
| Isopropanol | 5 | 5 | 5 | 5 | 5 | 5 | 5 | 5 | 5 |
| Glycolic Acid (70%) |  |  |  |  |  |  |  |  | 5 |

TABLE 9

Embodiments of Compositions of the Invention

|  | A | B | C | D | E | F | G | H | I | J | K | L |
|---|---|---|---|---|---|---|---|---|---|---|---|---|
| Water | 40 | 40 | 40 | 40 | 40 | 40 | 40 | 40 | 40 | 40 | 40 | 47.5 |
| Phosphoric acid (75%) | 40 | 40 | 40 | 40 | 40 | 40 | 40 | 40 | 40 | 40 | 40 | 35 |
| Lactic acid (88%) | 5 | 5 | 5 | 5 | 5 | 5 | 5 | 5 | 5 | 5 | 5 | 5 |
| Dequest 2000 LC | 3 | 3 | 3 | 3 | 3 | 3 | 3 | 3 | 3 | 3 | 3 | 3 |
| Tomah PA-14 | 2.5 | 2.5 | 2.5 | 2.5 | 2.5 | 2.5 | 2.5 | 2.5 | 2.5 | 2.5 | 2.5 | 2.5 |
| Isopropanol | 5 | 5 | 5 | 5 | 5 | 5 | 5 | 5 |  |  |  | 5 |
| Octanoic Acid | 2 | 2 | 2 | 2 | 2 | 2 | 2 | 2 | 2 | 2 | 2 | 2 |
| SXS (40%) |  |  |  |  |  |  |  |  | 5 | 5 | 5 |  |
| AO-455 | 2.5 |  |  |  |  |  |  |  | 2.5 |  |  |  |
| Alkoxylated Amine 7 |  | 2.5 |  |  |  |  |  |  |  |  | 2.5 |  |
| Alkoxylated Amine 6 |  |  | 2.5 |  |  |  |  |  |  |  |  |  |
| Alkoxylated Amine 8 |  |  |  | 2.5 |  |  |  |  |  |  |  |  |
| Tomah Q-17-2 pg |  |  |  |  | 2.5 |  |  |  |  |  |  |  |
| Tomah Q-17-2 ipa |  |  |  |  |  | 2.5 |  |  |  |  | 2.5 |  |
| Tomah Q-14-2 |  |  |  |  |  |  | 2.5 |  |  |  |  |  |
| Alkoxylated Amine 9 |  |  |  |  |  |  |  | 2.5 |  |  |  |  |

Results

Compositions 1-8 remained clear for at least 7 days at temperatures from 40 to 122° F. Under these conditions compositions 11 and 12 were predominantly slightly hazy. The results of these studies are shown in Tables 10 and 11. The compositions that had been aged at 122° F. were diluted to 2 wt-% use solutions and their appearance was noted. The use solution were predominantly hazy or slightly hazy. Composition 19 exhibited surprising effective antimicrobial activity.

TABLE 10

| Temperature | A | B | C | D | E | F | G | H |
|---|---|---|---|---|---|---|---|---|
| Control (RT) | | | | | | | | |
| initial | clear | clear | clear | clear | clear | clear | clear | clear |
| 24 hrs. | clear | clear | clear | clear | clear | clear | clear | clear |

TABLE 10-continued

| | | | | | | | | |
|---|---|---|---|---|---|---|---|---|
| 48 hrs. | clear | clear | clear | clear | clear | clear | clear | clear |
| 5 days | clear | clear | clear | clear | clear | clear | clear | clear |
| 40° F. | | | | | | | | |
| initial | clear | clear | clear | clear | clear | clear | clear | clear |
| 24 hrs. | clear | clear | clear | clear | clear | clear | clear | clear |
| 48 hrs. | clear | clear | clear | clear | clear | clear | clear | clear |
| 5 days | clear | clear | clear | clear | clear | clear | clear | clear |
| 122° F. | | | | | | | | |
| initial | clear | clear | clear | clear | clear | clear | clear | clear |
| 24 hrs. | clear | clear | clear | clear | clear | clear | clear | clear |
| 48 hrs. | clear | clear | clear | clear | clear | clear | clear | clear |
| 5 days | clear | clear | clear | clear | clear | clear | clear | clear |

TABLE 10-continued

| Temperature | I | J | K | L |
|---|---|---|---|---|
| Control (RT) | | | | |
| initial | separated cloudy | separated cloudy | vsh | vsh |
| 24 hrs. | not tested | not tested | vsh | vsh |
| 48 hrs. | not tested | not tested | vs flock | vsh |
| 5 days | not tested | not tested | vs sed | vsh |
| 40° F. | | | | |
| initial | separated cloudy | separated cloudy | vsh | vsh |
| 24 hrs. | not tested | not tested | vsh | vsh |
| 48 hrs. | not tested | not tested | vsh | vsh |
| 5 days | not tested | not tested | vs sed | vsh |
| 122° F. | | | | |
| initial | separated cloudy | separated cloudy | vsh | vsh |
| 24 hrs. | not tested | not tested | vsh | clear |
| 48 hrs. | not tested | not tested | vsh | clear |
| 5 days | not tested | not tested | vs sed | clear | vsh refers to very slightly hazy;
vs flock refers to very slightly flocculent;
vs sed refers to very slight sediment

TABLE 11

| | 1 | 2 | 3 | 4 | 5 | 6 | 7 | 8 | 9 |
|---|---|---|---|---|---|---|---|---|---|
| Concentrate stability | no | no | no | no | yes | no | yes | yes | yes |
| 2% soln appearance | nr | nr | nr | nr | clear | nr | slight haze | phase separation | phase separation |

| | 10 | 11 | 12 | 13 | 14 | 15 | 16 | 17 | 18 |
|---|---|---|---|---|---|---|---|---|---|
| Concentrate stability | yes | yes | yes | yes | yes | yes | yes | yes | yes |
| 2% soln appearance | hazy | clear | vvsh | phase separation | phase separation | vvsh | slight haze | clear | clear | vvsh refers to very very slight haze
nr refers to not run

TABLE 12

Antimicrobial Activity of Control Composition Lacking Alkoxylated Amine (Composition L). Activity reported as log kill after stated times.

| wt-% | Organism | T (° C.) | 5 min | 15 min | 30 min |
|---|---|---|---|---|---|
| 1 | Candida/Saccharomyces | 4.4 | 0.1 | 0.19 | 0.19 |
| 2 | Candida/Saccharomyces | 4.4 | 0.8 | 0.41 | 0.87 |
| 1 | Candida/Saccharomyces | 20 | 0.28 | 0.26 | 0.33 |
| 2 | Candida/Saccharomyces | 20 | 0.51 | 2.05 | 3.33 |
| 1 | P. parvulus/L. malefermentans | 4.4 | >6.89 | >6.89 | >6.89 |
| 2 | P. parvulus/L. malefermentans | 4.4 | >6.89 | >6.89 | >6.89 |
| 1 | A. pasterianus | 4.4 | 0.15 | 1.78 | 4.1 |
| 2 | A. pasterianus | 4.4 | 1.44 | >5.74 | >5.74 |

TABLE 13

Antimicrobial Activity of Composition According to the Present Invention (Test Composition 19). Activity reported as log kill after stated times.

| wt-% | Organism | T (° C.) | 5 min | 15 min | 30 min |
|---|---|---|---|---|---|
| 1 | Candida/Saccharomyces | 4.4 | 0.69 | 0.91 | 1.37 |
| 2 | Candida/Saccharomyces | 4.4 | 4.28 | 5.06 | 6.24 |
| 1 | Candida/Saccharomyces | 20 | 1.3 | 2.57 | 3.15 |
| 2 | Candida/Saccharomyces | 20 | >6.41 | >6.41 | >6.41 |
| 1 | P. parvulus/L. malefermentans | 4.4 | 6.05 | >7.18 | >7.18 |
| 2 | P. parvulus/L. malefermentans | 4.4 | >7.18 | >7.18 | >7.18 |
| 1 | P. parvulus/L. malefermentans | 20 | >7.18 | >7.18 | >7.18 |
| 2 | P. parvulus/L. malefermentans | 20 | >7.18 | >7.18 | >7.18 |
| 1 | A. pasterianus | 4.4 | 0.59 | 4.57 | >5.79 |
| 2 | A. pasterianus | 4.4 | >5.79 | >5.79 | >5.79 |
| 1 | A. pasterianus | 20 | 5.04 | >5.79 | >5.79 |
| 2 | A. pasterianus | 20 | >5.79 | >5.79 | >5.79 |

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

We claim:

1. A composition consisting of: about 5 to about 10 wt-% fatty acid antimicrobial agent; about 15 to about 30 wt-% alkoxylated amine the alkoxylated amine being:
   $C_{12}$ to $C_{14}$ propoxy amine ethoxylate of the formula: R—$(PO)_{10}$N$[EO]_{2.5}$—H$[EO]_{2.5}$—H;
   $C_{12}$ to $C_{14}$ propoxy amine ethoxylate of the formula: R—$(PO)_5$N$[EO]_{2.5}$—H$[EO]_{2.5}$—H;
   $C_{12}$ to $C_{14}$ propoxy amine ethoxylate of the formula: R—$(PO)_2$N$[EO]_{2.5}$—H$[E]_{2.5}$—H;
   poly (5) oxyethylene isodecyloxypropylamine, which has a branched $C_{10}H_{21}$ alkyl group off the ether oxygen;

iso-(2-hydroxyethyl) isodecyloxypropylamine, which has a branched $C_{10}H_{21}$ alkyl group off the ether oxygen; or mixtures thereof;

the alkoxylated amine and fatty acid antimicrobial agent being at a weight ratio of about 2.5:1 to about 3.5:1;

water;

wherein the composition is clear and has effective antimicrobial activity.

2. The composition of claim 1, wherein the carboxylic acid antimicrobial agent is a $C_6$-$C_{14}$ alkyl carboxylic acid, or salt or ester thereof.

3. The composition of claim 2, wherein the $C_6$-$C_{14}$ alkyl carboxylic acid is selected from the group consisting of octanoic acid, heptanoic acid, decanoic acid, dodecanoic acid, myristic acid, or mixture thereof.

4. The composition of claim 2, wherein the $C_8$-$C_{14}$ alkyl carboxylic acid is octanoic acid.

5. A method of reducing microbial population on an object, comprising contacting the object with a composition consisting of:

about 0.005 to about 20 fatty acid antimicrobial agent; and
about 0.1 to about 10 wt-% alkoxylated amine of Formula III:

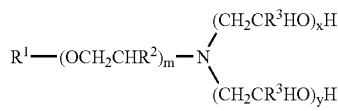

wherein $R^1$ is a straight or branched alkyl or alkylaryl; $R^2$ is independently in each occurrence hydrogen or alkyl from 1 to 6 carbons; $R^3$ is independently in each occurrence hydrogen or alkyl of from 1 to 6 carbons; m is about 1 to about 20; x and y is each independently 1 to about 20; and x+y averages from about 2 to about 40;

the alkoxylated amine and fatty acid antimicrobial agent being at a ratio of about 2.5:1 to about 3.5:1;

water;

wherein the composition is clear and has effective antimicrobial activity.

6. A composition consisting of:

about 1 to about 5 wt-% fat acid antimicrobial agent;
about 2 to about 12 wt-% alkoxylated amine of Formula III:

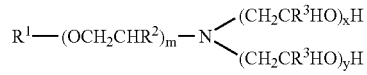

wherein $R^1$ is a straight or branched alkyl or alkylaryl; $R^2$ is independently in each occurrence hydrogen or alkyl from 1 to 6 carbons; $R^3$ is independently in each occurrence hydrogen or alkyl of from 1 to 6 carbons; m is about 1 to about 20; x and y is each independently 1 to about 20; and x+y averages from about 2 to about 40;

the alkoxylated amine and fatty acid antimicrobial agent being at a weight ratio of about 2.5:1 to about 3.5:1;

water;

wherein the composition is clear and has effective antimicrobial activity.

7. The composition of claim 6, wherein the ratio of alkoxylated amine and carboxylic acid antimicrobial agent is about 3:1.

8. The composition of claim 6, wherein the carboxylic acid is octanoic acid.

* * * * *